US009044518B2

(12) United States Patent
Pettit et al.

(10) Patent No.: US 9,044,518 B2
(45) Date of Patent: Jun. 2, 2015

(54) AURISTATIN TYRAMINE PHOSPHATE SALTS AND AURISTATIN AMINOQUINOLINE DERIVATIVES AND PRODRUGS THEREOF

(75) Inventors: George R. Pettit, Paradise Valley, AZ (US); Fiona Hogan, Gilbert, AZ (US); Steven Toms, Wellington (NZ)

(73) Assignee: ARIZONA BOARD OF REGENTS, A BODY CORPORATE OF THE STATE OF ARIZONA ACTING FOR AND ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 14/007,743

(22) PCT Filed: Mar. 29, 2012

(86) PCT No.: PCT/US2012/031118
§ 371 (c)(1),
(2), (4) Date: Sep. 26, 2013

(87) PCT Pub. No.: WO2012/135440
PCT Pub. Date: Oct. 4, 2012

(65) Prior Publication Data
US 2014/0023666 A1    Jan. 23, 2014

Related U.S. Application Data

(60) Provisional application No. 61/469,428, filed on Mar. 30, 2011.

(51) Int. Cl.
| *A61K 38/00* | (2006.01) |
| *A61K 47/48* | (2006.01) |
| *C07D 401/12* | (2006.01) |
| *C07D 207/12* | (2006.01) |
| *C07K 7/02* | (2006.01) |
| *G01N 33/50* | (2006.01) |
| *C07K 5/02* | (2006.01) |
| *A61K 45/06* | (2006.01) |
| *A61K 38/08* | (2006.01) |
| *A61K 31/4709* | (2006.01) |
| *A61K 31/472* | (2006.01) |

(52) U.S. Cl.
CPC ........ *A61K 47/48415* (2013.01); *C07D 401/12* (2013.01); *C07D 207/12* (2013.01); *C07K 7/02* (2013.01); *G01N 33/5014* (2013.01); *A61K 38/00* (2013.01); *C07K 5/0205* (2013.01); *A61K 45/06* (2013.01); *A61K 38/08* (2013.01); *A61K 31/4709* (2013.01); *A61K 31/472* (2013.01)

(58) Field of Classification Search
None
See application file for complete search history.

(56) References Cited

U.S. PATENT DOCUMENTS

| 5,583,024 | A | 12/1996 | McElroy et al. |
| 5,635,483 | A | 6/1997 | Pettit et al. |
| 5,665,860 | A | 9/1997 | Pettit et al. |
| 5,674,713 | A | 10/1997 | McElroy et al. |
| 5,700,670 | A | 12/1997 | Yamagishi et al. |
| 6,214,345 | B1 | 4/2001 | Firestone et al. |
| 6,602,677 | B1 | 8/2003 | Wood et al. |
| 6,884,869 | B2 | 4/2005 | Senter et al. |
| 7,098,308 | B2 | 8/2006 | Senter et al. |
| 7,256,257 | B2 | 8/2007 | Doronina et al. |
| 7,423,116 | B2 | 9/2008 | Doronina et al. |
| 7,498,298 | B2 | 3/2009 | Doronina et al. |
| 7,659,241 | B2 | 2/2010 | Senter et al. |
| 7,745,394 | B2 | 6/2010 | Doronina et al. |
| 7,829,531 | B2 | 11/2010 | Senter et al. |
| 7,851,437 | B2 | 12/2010 | Senter et al. |
| 7,964,566 | B2 | 6/2011 | Doronina et al. |
| 7,964,567 | B2 | 6/2011 | Doronina et al. |
| 7,994,135 | B2 | 8/2011 | Doronina et al. |
| 8,609,105 | B2 * | 12/2013 | Senter et al. ............... 424/179.1 |
| 2003/0083263 | A1 | 5/2003 | Doronina et al. |
| 2007/0269902 | A1 | 11/2007 | Beechem et al. |
| 2009/0047296 | A1 | 2/2009 | Doronina et al. |
| 2010/0303808 | A1 * | 12/2010 | Williams ................... 424/133.1 |
| 2011/0033378 | A1 * | 2/2011 | Dimasi et al. ................ 424/1.49 |
| 2011/0064753 | A1 | 3/2011 | Senter et al. |
| 2012/0003247 | A1 | 1/2012 | Doronina et al. |
| 2012/0003248 | A1 | 1/2012 | Doronina et al. |
| 2012/0027783 | A1 | 2/2012 | Doronina et al. |
| 2012/0027784 | A1 | 2/2012 | Doronina et al. |
| 2012/0034246 | A1 | 2/2012 | Doronina et al. |
| 2012/0034247 | A1 | 2/2012 | Doronina et al. |
| 2012/0141508 | A1 | 6/2012 | Doronina et al. |
| 2012/0141509 | A1 | 6/2012 | Doronina et al. |
| 2012/0141510 | A1 | 6/2012 | Doronina et al. |
| 2012/0148608 | A1 | 6/2012 | Doronina et al. |
| 2012/0148610 | A1 | 6/2012 | Doronina et al. |

OTHER PUBLICATIONS

Abernethy, J.L. and Kilday, W., "Behavior of Certain Pyridines, Quinolines, and Isoquinolines with Amino or Hydrazino Substituents Toward N-Acylamino Acids Under the Influence of Papain Catalysis", In Journal of Organic Chemistry, vol. 25, No. 11, Nov. 1960, pp. 1924-1928.
Banerjee, S., et al.,"Efficacy of Selected Natural Products as Therapeutic Agents against Cancer", In Journal of Natural Products, vol. 71, No. 3, Mar. 2008, 492-496.
Beresnevicius, Z.J., et al., "Interaction of Aminoquinolines with unsaturated carboxylic Acids", In Chemistry of Heterocylic Compounds, vol. 36, No. 4, Apr. 2000, pp. 432-438.
Bertho, J., et al., "Amino Acid Fluorides: Their preparation and use in peptide synthesis", In Tetrahedron Letters, vol. 32, No. 10, Mar. 1991, pp. 1303-1306.
Carpino, L.A., et al., "Peptide Synthesis via Amino Acid Halides", In Accounts of Chemical Research, vol. 29, Jun. 13, 1996, pp. 268-274.

(Continued)

*Primary Examiner* — Sheela J Huff
(74) *Attorney, Agent, or Firm* — Byrne Poh LLP; Nina R. Horan

(57) ABSTRACT

The present invention relates to new auristatin compounds and prodrugs thereof, compositions comprising them and uses thereof.

22 Claims, No Drawings

(56) References Cited

OTHER PUBLICATIONS

Carpino, L.A., et al., "tert-Butyloxycarbonyl and benzyloxycarbonyl amino acid fluorides. New, stable rapid-acting acylating agents for peptide synthesis" In The Journal of Organic Chemistry, vol. 56, No. 8, Apr. 1991, pp. 2611-2614.

Cree, I.A., et al., "Methotrexate chemosensitivity by ATP luminescence in human leukemia cell lines and in breast cancer primary cultures: comparison of the TCA-100 assay with a clonogenic assay", In AntiCancer Drugs, vol. 6, No. 3, Jun. 1995, pp. 398-404.

Crouch, S.P.M., et al., "The use of ATP bioluminescence as a measure of cell proliferation and cytotoxicity", In Journal of Immunol. Meth., vol. 160, No. 1, Mar. 1993, pp. 81-88.

Dalai, S. and Burchill, S.A., "Preclinical evaluation of vascular-disrupting agents in Ewing's sarcoma family of tumours", In European Journal of Cancer, vol. 45, No. 4, Mar. 2009, pp. 713-722.

DeVita, R.J., "Aminoquinoline Melanin-Concentrating Hormone 1-Receptor (MCH1-R) Antagonists", In Current Topics in Medicinal Chemistry, vol. 7, No. 15, Aug. 2007, pp. 1433-1439.

Doronina, S.O., et al., "Development of potent monoclonal antibody auristatin conjugates for cancer therapy", In Nature Biotechnology, vol. 21, No. 7, Jul. 2003, pp. 778-784.

Egan, T.J., et al., "Structure-Function Relationships in Aminoquinolines:? Effect of Amino and Chloro Groups on Quinoline-Hematin Complex Formation, Inhibition of β-Hematin Formation, and Antiplasmodial Activity", In Journal of Medicinal Chemistry, vol. 43, No. 2, Jan. 2000, pp. 283-291.

Fennell, B.J., et al., "Effects of the antimitotic natural product dolastatin 10, and related peptides, on the human malarial parasite *Plasmodium falciparum*", In Journal of Antimicrobial Chemotherapy, vol. 51, No. 4, Apr. 2003, pp. 833-841.

Furlong, S.T., et al., "Synthesis and physical characterization of a P1 arginine combinatorial library, and its application to the determination of the substrate specificity of serine peptidases", In Bioorgannic & Medicinal Chemistry, vol. 10, No. 11, Nov. 10, 2002, pp. 3637-3647.

Goda, F.E., et al., "Synthesis and biological evaluation of novel 6-nitro-5-substituted aminoquinolines as local anesthetic and antiarrhythmic agents: molecular modeling study", In Bioorganic medicinal chemistry, vol. 13, No. 9, May 2005, pp. 3175-3183.

Goodson, J.M., "Dental Applications", In Medical Applications of Controlled Release, CRC Press, vol. 2, Jan. 1984, pp. 115-138.

Hokland, S.L. and Horsman, M.R., "The new vascular disrupting agent combretastatin-A1-disodium-phosphate (OXi4503) enhances tumour response to mild hyperthermia and Thermoradiosensitization", In International Journal of Hypothermia, vol. 23, No. 7, Nov. 2007, pp. 599-606.

Horti, J., et al., "Phase I study of TZT-1027, a novel synthetic dolastatin 10 derivative, for the treatment of patients with non-small cell lung cancer", In Cancer Chemotherapy and Pharmacology, vol. 62, No. 1, Jun. 2008, pp. 173-180.

International Preliminary Report on Patentability dated Oct. 10, 2013 in International Application No. PCT/US2012/031118.

Kirwan, I.G., et al., "Comparative Preclinical Pharmacokinetic and Metabolic Studies of the Combretastatin Prodrugs Combretastatin A4 Phosphate and A1 Phosphate", In Clinical Cancer Research, vol. 10, No. 4, Feb. 15, 2004, pp. 1446-1453.

Kobayashi, M., et al., "Antitumor activity of TZT-1027, a novel dolastatin 10 derivative", In Japanese Journal of Cancer Research, vol. 88, Mar. 1997, pp. 316-327.

Kouznetsov, V.V. and Gomez-Barrio, A., "Recent development in the design and synthesis of hybrid molecules based on aminoquinoline ring and their antiplasmodial evaluation", In European Journal of Medicinal Chemistry, vol. 44, No. 8, Aug. 2009, pp. 3091-3113.

Langer, R., "New Methods of Drug Delivery", In Science, vol. 249, No. 4976, Sep. 28, 1990, pp. 1527-1533.

Lash, A., "Antibody-Drug Conjugates: The Next Generation of Moving Parts", In Start-Up, Dec. 2011, pp. 12-17.

Mamber, S.W., et al., "Tubulin polymerization by paclitaxel (taxol) phosphate prodrugs after metabolic activation with alkaline phosphatase", In Journal of Pharmacology and Experimental Therapeutics, vol. 274, No. 2, Aug. 1995, pp. 877-883.

Mordant, C., et al., "Total synthesis of dolastatin 10 through ruthenium-catalyzed asymmetric hydrogenations", In Tetrahedron, vol. 63, No. 27, Jul. 2, 2007, pp. 6115-6123.

Nanayakkara, N.P.D., et al., "Antiparasitic Activities and Toxicities of Individual Enantiomers of the 8-Aminoquinoline 8-[(4-Amino-1-Methylbutyl)Amino]-6-Methoxy-4-Methyl-5-[3,4-Dichlorophenoxy]Quinoline Succinate", In Antimicrobial Agents Chemotherapy, vol. 52, No. 6, Jun. 2008, pp. 2130-2137.

Olah, G.A., et al., "Synthetic Methods and Reactions; IV. Fluorination of Carboxylic Acids with Cyanuric Fluoride", In Synthesis, No. 8, Aug. 1973, pp. 487-488.

Patterson, D.M., et al., "Combretastatin A-4 Phosphate-Vascular disrupting agent, Oncolytic, Treatment of age-related macular degeneration" , In Drugs of the Future, vol. 32, No. 12, Dec. 2007, pp. 1025-1032.

Pettit, G.R. and Grealish, M.P., "A cobalt-phosphine complex directed Reformatsky approach to a stereospecific synthesis of the dolastatin 10 unit dolaproine (Dap)", In Journal of Organic Chemistry, vol. 66, No. 25, Dec. 2001, pp. 8640-8642.

Pettit, G.R., "Dolastatin Anticancer Drugs", in International Oncology Updates: Marine Anticancer Compounds in the Era of Targeted Therapies, 2009, pp. 19-49.

Pettit, G.R., "The Dolastatins", In Progress in the Chemistry of Organic Natural Products, vol. 70, Jan. 1997, pp. 2-70.

Pettit, G.R., et al., "Antineoplastic agents 337. Synthesis of dolastatin 10 structural modifications", In Anti-Cancer Drug Design, vol. 10, No. 7, Oct. 1995, pp. 529-544.

Pettit, G.R., et al., "20 Antineoplastic Agents 365. Dolastatin 10 SAR Probes", In Anti-Cancer Drug Design, vol. 13, No. 4, Jun. 1998, pp. 243-277.

Pettit, G.R., et al., "Antineoplastic agents 389. New syntheses of the combretastatin A-4 prodrug", In Anti-Cancer Drug Design, vol. 13, No. 3, Apr. 1998, pp. 183-191.

Pettit, G.R., et al., "Antineoplastic Agents. 511. Direct Phosphorylation of Phenpanstatin and Pancratistatin", In Journal of Natural Products, vol. 67, No. 3, Mar. 2004, pp. 322-327.

Pettit, G.R., et al., "Dolastins 24. Synthesis of (−)-dolastin 10. X-Ray molecular structure of N,N-dimethylvalyl-valyl-dolaisoleuine tert-butyl ester", In Journal of the Chemical Society, Perkin Transactions 1, No. 8, Apr. 1996, pp. 859-863.

Pettit, G.R., et al., "Progress in the Chemistry of Organic Natural Products", 1st edition, vol. 70, Springer-Verlag/Wein, Jan. 1997, pp. 1-79.

Pettit, G.R., et al., "The Dolastatins. 17. Synthesis of Dolaproine and Related Diastereoisomers", In Journal of Organic Chemistry, vol. 59, No. 21, Oct. 1994, pp. 6287-6295.

Pettit, G.R., et al., "The isolation and structure of a remarkable marine animal antineoplastic constituent: dolastatin 10", In Journal of the American Chemical Society, vol. 109, No. 22, Oct. 1987, pp. 6883-6885.

Pettit, G.R., et al., "Antineoplastic agents 429. Syntheses of the combretastatin A-1 and combretastatin B-1 prodrugs", In Anti-Cancer Drug Design, vol. 15, No. 3, Jun. 2000, pp. 203-216.

Pfister, J.R., "Isolation and Bioactivity of 2-Aminoquinoline from *Leucopaxillus albissimus*", in Journal of Natural Products, vol. 51, No. 5, Sep. 1988, pp. 969-970.

Pozdnev, V.F., "Activation of carboxylic acids by pyrocarbonates. Synthesis of arylamides of N-protected amino acids and small peptides using dialkyl pyrocarbonates as condensing reagents", International Journal of Peptide & Protein Research, vol. 44, No. 1, Jul. 1994, pp. 36-48.

Saulnier, M.G., et al., "Synthesis of Etoposide phosphate, BMY-40481: A Water-Soluble clinically active prodrug of etoposide", In Bioorganic and Medicinal Chemistry Letters, vol. 4, No. 21, Nov. 10, 1994, pp. 2567-2572.

Schulman, S.G., et al., "PhotoLuminescence of 6- and 7-Aminoquinolines", In Analytica Chimica Acta, vol. 65, No. 1, Jun. 1973, pp. 59-67.

Shao, Y., et al., "Steric effect on the nuclease activity of Cu(II) complexes with aminoquinoline derivatives," In Journal of Inorganic Biochemistry, vol. 99, No. 7, Jul. 2005, pp. 1490-1496.

(56) References Cited

OTHER PUBLICATIONS

Sheridan, R.E. "Structural Features of Aminoquinolines necessary for antagonist activity against botulinum neurotoxin", In Toxicon, vol. 35, No. 9, Sep. 1997, pp. 1439-1451.

Shnyder, S.D., et al., "Auristatin PYE, a novel synthetic derivative of dolastatin 10, is highly effective in human colon tumour models", In International Journal of Oncology, vol. 31, No. 2, Aug. 2007, pp. 353-360.

Temming, K. et al., "Evaluation of RGD-Targeted Albumin Carriers for Specific Delivery of Auristatin E to Tumor Blood Vessels", In Bioconjugate Chemistry, vol. 17, No. 6, Nov.-Dec. 2006, pp. 1385-1394.

Temming, K., et al., "Improved Efficacy of alphavbeta3-Targeted Albumin Conjugates by Conjugation of a Novel Auristatin Derivative" In Molecular Pharmaceutics, vol. 4, No. 5, Sep.-Oct. 2007, pp. 686 694.

Vale, Ni., "Primaquine revisted six decdes after its discovery", In European Journal of Medicinal Chemistry, vol. 44, No. 3, Mar. 2009, pp. 937-953.

Watanabe, J., et al., "Antitumor Activity of TZT-1027 (Soblidotin)", In Anticancer Research, vol. 26, No. 3A, May-Jun. 2006, pp. 1973-1981.

Wenschuh, H., et al., "Peptide Assembly in the absence of Base via Fmoc Amino Acid Fluorides", In Journal of the Chemical Society, Chemical Communications, vol. 1995, No. 6, Mar. 1995, pp. 669-670.

Woyke, T., et al., "Differential Gene Expression in Auristatin PHE-Treated *Cryptococcus neoformans*", In Antimicrobial Agents and Chemotherapy, vol. 48, No. 2, Feb. 2004, pp. 561-567.

\* cited by examiner

AURISTATIN TYRAMINE PHOSPHATE SALTS AND AURISTATIN AMINOQUINOLINE DERIVATIVES AND PRODRUGS THEREOF

CROSS REFERENCE TO RELATED APPLICATIONS

This application is a national stage application under 35 U.S.C. §371 of International Application No. PCT/US12/31118, filed Mar. 29, 2012, which claims the benefit U.S. Provisional Application No. 61/469,428, filed Mar. 30, 2011, each of which is incorporated by reference herein in their entireties.

FEDERALLY SPONSORED RESEARCH OR DEVELOPMENT

This invention was made with government support from grants R01 CA 90441-01-05, 2R56 CA 090441-06A1, and 5-R01 CA 90441-07-08 awarded by the Division of Cancer Treatment and Diagnosis, National Cancer Institute, DHHS. The government has certain rights in the invention.

FIELD OF THE INVENTION

The present invention relates to new auristatin compounds and prodrugs thereof, compositions comprising them and uses thereof.

BACKGROUND OF THE INVENTION

The remarkable anticancer properties of dolastatin 10 (1), a unique pentapeptide that was isolated by one of the present inventors from the sea hare *Dolabella auricularia*, has led to intense interest in closely related derivatives (auristatins) that are suitable for clinical trial. Such structural modifications have provided a number of potential clinical candidates with enhanced efficacy and pharmacological characteristics. Replacement of the dolaphenine (Doe) unit with phenethylamides to give auristatins PE (2a), PHE (2b) and E (2c) and with pyridylethylamide (auristatin PYE) has led to active analogues that are undergoing preclinical and clinical development.

Dolastatin 10 and three of the auristatins are in human cancer clinical trials, ranging from phase I to phase III and N-des-methyl-auristatin E linked to a CD-30 monoclonal antibody is in marketing as ADCETRIS™.

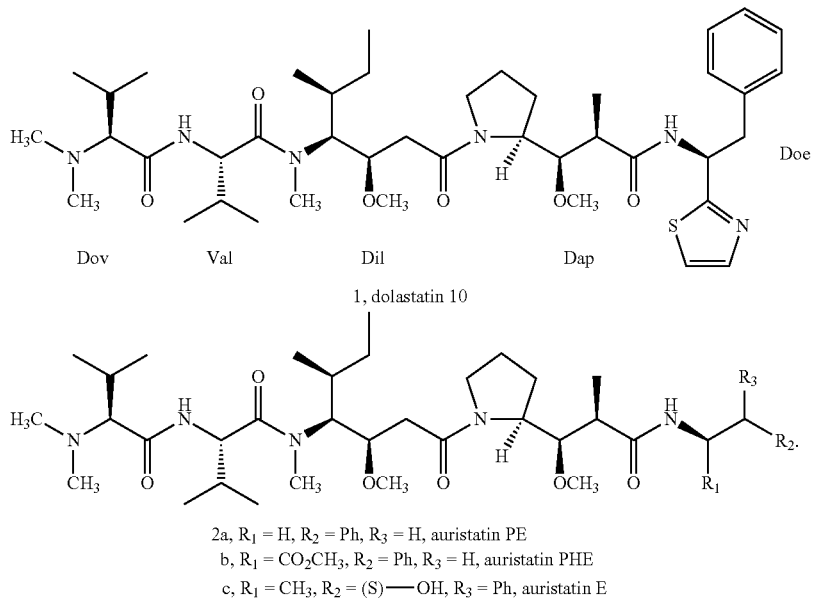

2a, $R_1$ = H, $R_2$ = Ph, $R_3$ = H, auristatin PE
b, $R_1$ = $CO_2CH_3$, $R_2$ = Ph, $R_3$ = H, auristatin PHE
c, $R_1$ = $CH_3$, $R_2$ = (S)—OH, $R_3$ = Ph, auristatin E Because of the potency of auristatins, they may be delivered linked to a monoclonal antibody. The linker to the monoclonal antibody is stable in extracellular fluid, but is cleaved once the conjugate has entered a tumor cell, thus activating the antimitotic mechanism at the site where it is most needed. In this way, antibody-drug conjugates (ADCs) made with auristatin antimitotic agents have been recognized as having significant preclinical and clinical oncology activity. SGN-75 is in clinical trials and is composed of an anti-CD70 antibody conjugated to monomethylauristatin F through a noncleavable maleimidocaproyl linkage.

Conjugation of auristatin drugs to antibodies, either directly or indirectly through linkers, involves consideration of a variety of factors, including the identity and location of the chemical group for conjugation of the drug, the mechanism of drug release, the structural elements providing drug release, and the structural modification to the released free drug. In addition, if the drug is to be released after antibody internalization, the mechanism of drug release must be consonant with the intracellular trafficking of the conjugate.

Given the promising results of SGN-75 as an agent as a therapeutic agent in clinical trials, there is a need to identify additional such agents for therapy.

BRIEF SUMMARY OF THE INVENTION

The present invention relates to new auristatin compounds and prodrugs thereof. The compounds are represented by formula (I):

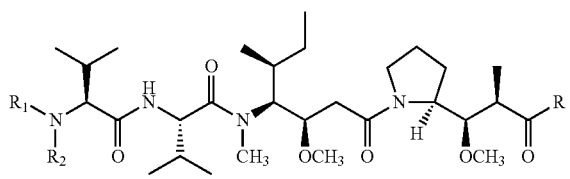

(I)

wherein R is selected from the group consisting of:

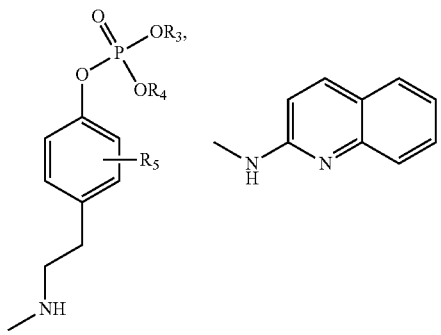

$R_1$ and $R_2$ are independently selected from the group consisting of H, alkyl, alkenyl, alkynyl and a Linker Unit;

$R_3$ and $R_4$ are independently selected from the group consisting of lithium ($Li^+$), sodium ($Na^+$), potassium ($K^+$), hydrogen (H), morpholine, quinine, tris(hydroxymethyl)aminomethane (TRIS), serine, nitroarginine and a Linker Unit; and each $R_5$ is selected from the group consisting of H, alkyl, alkenyl, alkynyl and a Linker Unit.

In preferred embodiments, R is:

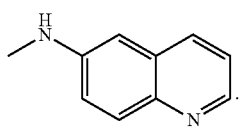

In other preferred embodiments, R is:

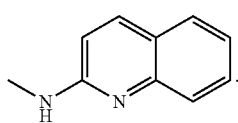

In other preferred embodiments, R is:

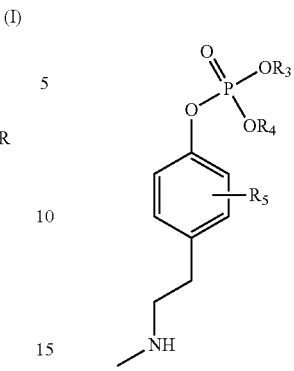

wherein, $R_3$ and $R_4$ are independently selected from the group consisting of lithium ($Li^+$), sodium ($Na^+$), potassium ($K^+$), hydrogen (H), morpholine, quinine, tris(hydroxymethyl)aminomethane (TRIS), serine, nitroarginine and a Linker Unit; and each $R_5$ is selected from the group consisting of H, alkyl, alkenyl, alkynyl and a Linker Unit.

In preferred embodiments, $R_1$ and $R_2$ are independently alkyl or a Linker Unit. Preferably, $R_1$ and $R_2$ are methyl. In other preferred embodiments, one of $R_1$ and $R_2$ is a Linker Unit.

In preferred embodiments, $R_3$ and $R_4$ are sodium ($Na^+$). In other preferred embodiments, one of $R_3$ and $R_4$ is a Linker Unit.

In preferred embodiments, each $R_5$ is H.

In some embodiments, the compounds of formula (I) may be conjugated to an antibody. In some embodiments, the compounds of formula (I) are conjugated through $R_3$ or $R_4$. In other embodiments, the compounds of formula (I) are conjugated through $R_1$ or $R_2$. In yet other embodiments, the compounds of formula (I) are conjugated through $R_5$.

The compound may be conjugated to the antibody directly or indirectly through a Linker Unit.

The present invention also relates to pharmaceutically acceptable salts or solvates of the compounds of formula (I).

The present invention also relates to a pharmaceutical composition comprising a compound of formula (I) or a pharmaceutically acceptable salt or solvate thereof, and a pharmaceutically acceptable carrier. The compound may be selected from any of the compounds described above.

In some embodiments, the pharmaceutical composition comprises a combination of compounds of formula (I) or pharmaceutically acceptable salts or solvates thereof and a pharmaceutically acceptable carrier.

In some embodiments, the pharmaceutical composition further comprises a therapeutically effective amount of a chemotherapeutic agent. The chemotherapeutic agent may be selected from the group consisting of a tubulin-forming inhibitor, a topoisomerase inhibitor, and a DNA binder.

The present invention also relates to methods of using the compounds of the present invention or pharmaceutical compositions thereof as auristatin prodrugs. The compound and pharmaceutical composition thereof may be selected from any of those described above.

In some embodiments, the present invention provides a method of killing or inhibiting the proliferation of tumor cells or cancer cells, comprising contacting the tumor cells or cancer cells with a compound of formula (I), or a pharmaceutically acceptable salt or solvate thereof, in an amount effective to kill or inhibit the proliferation of the tumor cells or cancer cells. In some embodiments, the method may further comprise contacting the cells with an effective amount of a chemotherapeutic agent.

In some embodiments, the present invention provides a method for killing or inhibiting the replication of a cell that produces an autoimmune disease. The method comprises contacting the cell with a compound of formula (I), or a pharmaceutically acceptable salt or solvate thereof, in an amount effective to kill or inhibit the replication of the cell.

In additional embodiments, the present invention provides a method of determining inhibition of cellular proliferation by a compound of formula (I), comprising: contacting cells in a cell culture medium to the compound, and measuring cytotoxic activity of the compound, whereby proliferation of the cells is inhibited. The methods may optionally further comprise culturing the cells for a period from about 6 hours to about 5 days.

In another embodiment, the present invention provides a method of measuring cell viability in the presence of a compound of formula (I). The method comprises contacting cells in a cell culture medium with the compound of formula (I), culturing the cells for a period from about 6 hours to about 5 days, preferably 96 hours; and measuring cell viability.

In another embodiment, the present invention provides a method for treating cancer in a patient comprising administering to the patient a compound of formula (I), or a pharmaceutically acceptable salt or solvate thereof, in an amount effective to treat cancer. In some embodiments, the method may further comprise administering to the patient an effective amount of a chemotherapeutic agent.

In additional embodiments, the present invention provides a method of inhibiting the growth of tumor cells that overexpress a tumor-associated antigen in a patient, comprising administering to the patient a compound of formula (I) conjugated to an antibody that is specific for the tumor-associated antigen, wherein the compound is administered in an amount effective to inhibit the growth of tumor cells in the patient. The method may optionally further comprise administering to the patient a chemotherapeutic agent in an amount effective to inhibit the growth of tumor cells in the patient.

In some embodiments, the compound may sensitize the tumor cells to the chemotherapeutic agent. In some embodiments, the compound may induce cell death. In other embodiments, the compound may induce apoptosis.

In another embodiment, the present invention provides a method for treating an autoimmune disease in a patient, comprising administering to the patient a compound of formula (I), or a pharmaceutically acceptable salt or solvate thereof, in an amount effective to treat the autoimmune disease.

In another embodiment, the present invention provides a method for treating an infectious disease in a patient, comprising administering to the patient a compound of formula (I), or a pharmaceutically acceptable salt or solvate thereof, in an amount effective to treat the infectious disease.

In some of the methods of the present invention, the compound of formula (I) is administered to a patient intravenously. In certain embodiments, the compound is formulated in a unit dosage injectable form.

In preferred embodiments of the methods of the present invention, the patient is a human.

In the cancer therapy methods of the invention, the cancer may be any cancer, including but not limited to, a cancer selected from the group consisting of breast, ovarian, stomach, endometrial, salivary gland, lung, kidney, colon, colorectal, thyroid, pancreatic, prostate and bladder cancer.

The present invention also relates to uses of the compound of formula (I) in the manufacture of a medicament for treating cancer, an autoimmune disease or an infectious disease.

In additional embodiments, the present invention provides an article of manufacture comprising a compound of formula (I), a container, and a package insert or label indicating that the compound can be used to treat cancer characterized by the overexpression of at least one tumor-associated antigen. The compound may be selected from any of the compounds described above.

DETAILED DESCRIPTION OF THE INVENTION

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The term "a" or "an" may mean more than one of an item.

The terms "and" and "or" may refer to either the conjunctive or disjunctive and mean "and/or".

The term "about" means within plus or minus 10% of a stated value. For example, "about 100" would refer to any number between 90 and 110.

The present invention provides new auristatin compounds and prodrugs thereof. The compounds are represented by formula (I):

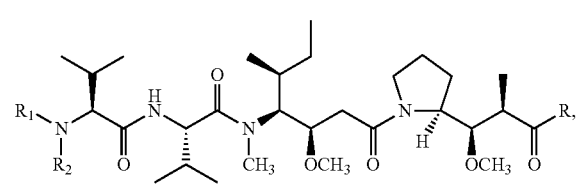

wherein R is selected from the group consisting of:

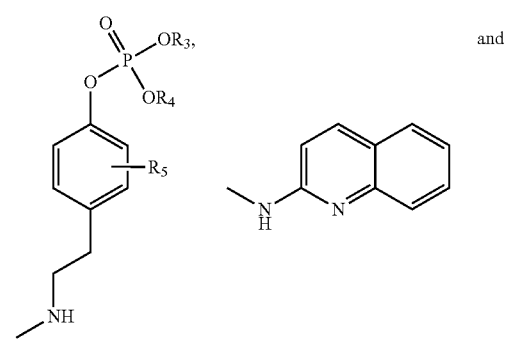

and

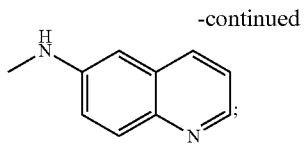

$R_1$ and $R_2$ are independently selected from the group consisting of H, alkyl, alkenyl, alkynyl and a Linker Unit;

$R_3$ and $R_4$ are independently selected from the group consisting of lithium ($Li^+$), sodium ($Na^+$), potassium ($K^+$), hydrogen (H), morpholine, quinine, tris(hydroxymethyl)aminomethane (TRIS), serine, nitroarginine and a Linker Unit; and each $R_5$ is selected from the group consisting of H, alkyl, alkenyl, alkynyl and a Linker Unit.

As used herein, the term "alkyl" refers to both straight and branched chains containing one to twelve carbon atoms. The terms "alkenyl" and "alkynyl" include both straight and branched chains containing two to twelve carbon atoms.

The term "Linker Unit," refers to a chemical moiety comprising a covalent bond or a chain of atoms that covalently attaches an antibody to a compound of formula (I). Suitable Linker Units are known in the art and include those disclosed in U.S. Pat. No. 7,745,394. Such Linker Units include, but are not limited to, a divalent radical such as an alkyldiyl, an aryldiyl, a heteroaryldiyl, moieties such as: —$(CR_2)_n$—, $O(CR_2)_n$—, repeating units of alkyloxy (e.g., polyethylenoxy, PEG, polymethyleneoxy) and alkylamino (e.g., polyethyleneamino, Jeffamine™); and diacid ester and amides including succinate, succinamide, diglycolate, malonate, and caproamide. See U.S. Pat. No. 7,745,394, at col. 39, lines 20-26.

The Linker Unit has formula:

$A_aW_wY_y$, 

wherein A is a Stretcher Unit,
a is 0 or 1,
each —W— is independently an Amino Acid Unit,
w is an integer ranging from 0 to 12,
Y is a Spacer Unit, and
y is 0, 1 or 2. See U.S. Pat. No. 7,745,394, at col. 63, lines 55-65.

The Stretcher Unit (-A-), when present, is capable of linking an antibody to an Amino Acid Unit (—W—). See U.S. Pat. No. 7,745,394, at col. 64, lines 2-17. The antibody has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the antibody functional groups are sulfhydryl and amino. Sulfhydryl groups can be generated by reduction of an intramolecular disulfide bond of an antibody. Alternatively, sulfhydryl groups can be generated by reaction of an amino group of a lysine moiety of an antibody using 2-iminothiolane (Traut's reagent) or another sulfhydryl generating reagent.

The Amino Acid Unit (—W—), when present, links the Stretcher Unit to the Spacer Unit if the Spacer Unit is present, links the Stretcher Unit to the compound of formula (I) if the Spacer Unit is absent, and links the antibody to the compound of formula (I) if the Stretcher Unit and Spacer Unit are absent. See U.S. Pat. No. 7,745,394, at col. 66, lines 15-22.

$W_w$— is a dipeptide, tripeptide, tetrapeptide, pentapeptide, hexapeptide, heptapeptide, octapeptide, nonapeptide, decapeptide, undecapeptide or dodecapeptide unit. The Amino Acid may be any amino acid. In some embodiments, the Amino Acid Unit comprises natural amino acids. In other embodiments, the Amino Acid Unit comprises non-natural amino acids.

The Spacer Unit (—Y—), when present, links an Amino Acid Unit to the compound of formula (I) when an Amino Acid Unit is present. See U.S. Pat. No. 7,745,394, at col. 69, lines 2-7. Alternately, the Spacer Unit links the Stretcher Unit to the compound of formula (I) when the Amino Acid Unit is absent. The Spacer Unit also links the compound of formula (I) to the antibody when both the Amino Acid Unit and Stretcher Unit are absent.

Suitable Spacer Units include, but are not limited to a glycine-glycine unit; a glycine unit; p-aminobenzyl alcohol (PAB) unit or aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals; spacers that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867); and a branched bis(hydroxymethyl)styrene (BHMS) unit.

In preferred embodiments of the compound of formula (I), R is:

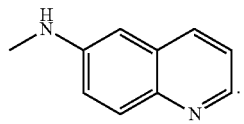

In other preferred embodiments, R is:

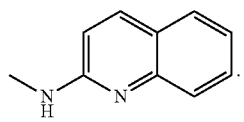

In other preferred embodiments, R is:

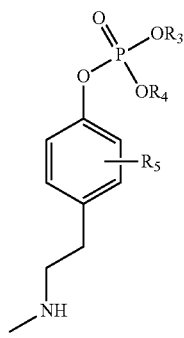

wherein, $R_3$ and $R_4$ are independently selected from the group consisting of lithium ($Li^+$), sodium ($Na^+$), potassium ($K^+$), hydrogen (H), morpholine, quinine, TRIS, serine, nitroarginine and a Linker Unit; and each $R_5$ is selected from the group consisting of H, alkyl, alkenyl, alkynyl and a Linker Unit.

In the latter preferred embodiments, the compounds of formula (I) are in the form of water-soluble phosphate salts and as such, are prodrugs. The synthesis of auristatins suitable for formulation of such salts is of considerable interest because the use of water-soluble phosphate derivatives has increased the bioavailability of a number of anticancer drugs, including combretastatins A-1 and A-4, pancratistatin, taxol and etoposide. The salts are dephosphorylated by serum phosphatases to yield the active drug, which is then transported intracellularly. Advantageously, these compounds can be delivered without the need for conjugation to a macromolecule, such as an antibody.

In preferred embodiments when the compounds of formula (I) are in the form of phosphate salts, $R_3$ and $R_4$ are sodium ($Na^+$). In other preferred embodiments, one of $R_3$ or $R_4$ is a Linker Unit.

In preferred embodiments, each $R_5$ is H. In other preferred embodiments, one $R_5$ is a Linker Unit and the others are H.

In preferred embodiments, $R_1$ and $R_2$ are independently alkyl or a Linker Unit. Preferably, $R_1$ and $R_2$ are methyl. In other preferred embodiments, one of $R_1$ or $R_2$ is a Linker Unit.

Preferred compounds of formula (I) are represented below in Table 1.

TABLE 1

| Compd. No. | R | $R_1$ | $R_2$ | $R_3$ | $R_4$ | $R_5$ |
|---|---|---|---|---|---|---|
| 3a | (phosphate-phenyl-ethyl-NH structure) | $CH_3$ | $CH_3$ | $Li^+$ | $Li^+$ | H |
| 3b | (phosphate-phenyl-ethyl-NH structure) | $CH_3$ | $CH_3$ | $Na^+$ | $Na^+$ | H |
| 3c | (phosphate-phenyl-ethyl-NH structure) | $CH_3$ | $CH_3$ | $K^+$ | $K^+$ | H |

TABLE 1-continued
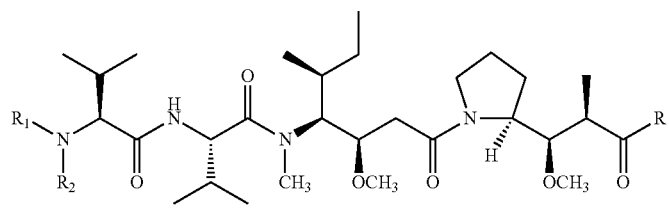
| Compd. No. | R | R₁ | R₂ | R₃ | R₄ | R₅ |
|---|---|---|---|---|---|---|
| 3d | ![phosphate-phenyl-ethyl-NHMe group with OR₃, OR₄, R₅] | CH₃ | CH₃ | H | morpholine | H |
| 3e | ![phosphate-phenyl-ethyl-NHMe group with OR₃, OR₄, R₅] | CH₃ | CH₃ | H | quinine | H |
| 3f | ![phosphate-phenyl-ethyl-NHMe group with OR₃, OR₄, R₅] | CH₃ | CH₃ | H | TRIS | H |
| 3g | ![phosphate-phenyl-ethyl-NHMe group with OR₃, OR₄, R₅] | CH₃ | CH₃ | H | serine | H |

TABLE 1-continued

| Compd. No. | R | $R_1$ | $R_2$ | $R_3$ | $R_4$ | $R_5$ |
|---|---|---|---|---|---|---|
| 3h | [phosphate-phenethyl-NH-methyl group with OR$_3$, OR$_4$, R$_5$ substituents] | CH$_3$ | CH$_3$ | H | nitroarginine | H |
| 4 | [N-methyl-2-aminoquinoline] | CH$_3$ | CH$_3$ | — | — | — |
| 5 | [N-methyl-6-aminoquinoline] | CH$_3$ | CH$_3$ | — | — | — |

In some embodiments, the compound of formula (I) is conjugated directly or indirectly to an antibody and as such, is a prodrug. The compound may be conjugated to an antibody through a Linker Unit at $R_1$, $R_2$, $R_3$, $R_4$ or $R_5$. The Linker Unit can operate to provide a suitable release of the compound of formula (I). The preparation of antibody drug conjugates is known to those of skill in the art.

The term "antibody" herein is used in the broadest sense and specifically covers intact monoclonal antibodies, polyclonal antibodies, monospecific antibodies, multispecific antibodies (e.g., bispecific antibodies), and antibody fragments that exhibit the desired biological activity. See U.S. Pat. No. 7,498,298, at col. 21, lines 21-26. An antibody may be of any type or class (e.g., IgG, IgE, IgM, IgD, and IgA) or subclass (e.g., IgG1, IgG2, IgG3, IgG4, IgA1 and IgA2). The antibody may be derived from any suitable species. In some embodiments, the antibody is of human or murine origin. An antibody may be, for example, human, humanized or chimeric.

The terms "specifically binds" and "specific binding" refer to antibody binding to a predetermined antigen. Typically, the antibody binds with an affinity of at least about $1 \times 10^7$ M$^{-1}$, and binds to the predetermined antigen with an affinity that is at least two-fold greater than its affinity for binding to a non-specific antigen (e.g., BSA, casein) other than the predetermined antigen or a closely-related antigen.

The term "monoclonal antibody" as used herein refers to an antibody obtained from a population of substantially homogeneous antibodies and thus, the individual antibodies are identical except for possible naturally occurring mutations that may have occurred. Monoclonal antibodies are highly specific and are directed against a single antigenic site. See U.S. Pat. No. 7,498,298, at col. 21, line 66-col. 22, line 5.The modifier "monoclonal" is not to be construed as requiring production of the antibody by any particular method. See U.S. Pat. No. 7,498,298, at col. 22, lines 12-16.

The term "monoclonal antibodies" specifically includes "chimeric" antibodies. A chimeric antibody refers to an antibody in which a portion of the heavy and/or light chain is identical to or homologous with a corresponding sequence of an antibody derived from a particular species or belonging to a particular antibody class or subclass and the remainder of the chain(s) is identical to or homologous with a corresponding sequences of an antibody derived from another species or belonging to another antibody class or subclass, as well as fragments thereof exhibiting the desired biological activity. See U.S. Pat. No. 7,498,298, at col. 22, lines 25-34.

The compounds of formula (I) may be conjugated to any antibody, e.g., an antibody that binds at least one of CD19, CD20, CD30, CD33, CD70, BCMA, Glypican-3, Liv-1 and Lewis Y antigen.

In another embodiment, the compound of formula (I) may be conjugated to an antibody that is immunospecific for the treatment of autoimmune diseases. Useful antibodies include, but are not limited to, anti-nuclear antibody; anti-dsDNA; anti-ssDNA, anti-cardiolipin antibody IgM, IgG; anti-phospholipid antibody IgM, IgG; anti-SM antibody; anti-mitochondrial antibody; thyroid antibody; microsomal antibody; thyroglobulin antibody; anti-SCL-70 antibody; anti-Jo antibody; anti-U1RNP antibody; anti-La/SSB antibody; anti-SSA; anti-SSB antibody; anti-perital cells antibody; anti-histones antibody; anti-RNP antibody; C-ANCA antibody; P-ANCA antibody; anti-centromere antibody; antifibrillarin antibody and anti-GBM antibody. See U.S. Pat. No. 7,498,298, at col. 82, lines 51-61.

In other embodiments, the antibodies can bind to a receptor or a receptor complex expressed on an activated lymphocyte. For example, the antibody binds to an activated lymphocyte that is associated with an autoimmune disease.

In other embodiments, the compound of formula (I) may be conjugated to an antibody that is immunospecific for a viral or a microbial antigen. The antibodies may be chimeric, humanized or human monoclonal antibodies. As used herein, the term "viral antigen" includes, but is not limited to, any viral peptide, polypeptide, protein (e.g., HIV gp120, HIV nef, RSV F glycoprotein, influenza virus neuraminidase, influenza virus hemagglutinin, HTLV tax, herpes simplex virus glycoprotein (e.g., gB, gC, gD, and gE) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungal, pathogenic protozoan, or yeast polypeptide including, e.g., LPS and capsular polysaccharide ⅝) that is capable of eliciting an immune response. See U.S. Pat. No. 7,498,298, at col. 83, lines 16-31.

Other useful antibodies include, but are not limited to, antibodies against the antigens from pathogenic strains of bacteria (*Streptococcus pyogenes, Streptococcus pneumoniae, Neisseria gonorrhoeae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter* (Vibrio)*fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma* spp., *Rickettsia prowazeki, Rickettsia tsutsugumushi,* and *Chlamydia* spp.); pathogenic fungi (*Coccidioides immitis, Aspergillus fumigatus, Candida albicans, Blastomyces dermatitidis, Cryptococcus neoformans,* and *Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or helminths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium,* and hookworms). See U.S. Pat. No. 7,498,298, at col. 83, lines 58-23.

Other useful antibodies include, but are not limited to, antibodies against antigens of pathogenic viruses, including as examples and not by limitation: Poxyiridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus. See U.S. Pat. No. 7,498,298, at col. 84, lines 24-35.

The compounds of this invention may be prepared by methods known to those skilled in the art for analogous compounds, as illustrated by the preparative examples that follow.

According to another embodiment, the present invention provides a pharmaceutical composition comprising a compound of formula (I) or a pharmaceutically acceptable salt or solvate thereof and a pharmaceutically acceptable carrier.

The phrase "pharmaceutically acceptable salt," as used herein, refers to pharmaceutically acceptable organic or inorganic salts of a compound (e.g., a drug, a drug attached to a linker (i.e., a drug-linker compound), or a drug-linker attached to a ligand or an antibody). The phrase includes acid additions salts, which can be formed with an amino group on the compound of formula (I). Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may include an acetate ion, a succinate ion or other counter ion. The counter ion may be any organic or inorganic moiety that stabilizes the charge on the parent compound. Furthermore, a pharmaceutically acceptable salt may contain more than one charged atom and more than one counter ion. See U.S. Pat. No. 7,498,298, at col. 42, lines 5-31.

The term "pharmaceutically acceptable carrier" refers to a diluent, adjuvant or excipient, with which a compound of the invention may be administered. Pharmaceutically acceptable carriers include any and all solvents, diluents, or other liquid vehicles, dispersions or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Examples of pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil;

safflower oil; sesame oil; olive oil; corn oil and soybean oil; glycols, such a propylene glycol or polyethylene glycol; esters, such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutically acceptable carrier may be solid or particulate, so that the compositions are, for example, in tablet or powder form. The carrier(s) can be liquid.

The pharmaceutical compositions of the present invention may optionally further comprise a pharmaceutical agent used in the treatment of cancer, an autoimmune disease or an infectious disease. In some embodiments, the compositions further comprise a chemotherapeutic agent in a therapeutically effective amount. The chemotherapeutic agent may be selected from the group consisting of a tubulin-forming inhibitor, a topoisomerase inhibitor, and a DNA binder.

The term "therapeutically effective amount" refers to an amount of a compound of formula (I) effective to treat a disease or disorder in a patient. In the case of cancer, the therapeutically effective amount of the compound may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the compound may inhibit the growth of and/or kill existing cancer cells, it may be cytostatic and/or cytotoxic. For cancer therapy, efficacy can, for example, be measured by assessing the time to disease progression (TTP) and/or determining the response rate (RR). See U.S. Pat. No. 7,498,298, at col. 28, lines 31-44.

The pharmaceutical compositions may be formulated for administration in the form of a solid or liquid and adapted for parenteral, ocular and intra-tumor administration. Parenteral administration includes subcutaneous injections, intravenous, intramuscular or intrasternal injection or infusion techniques. In one aspect, the compositions are administered parenterally. In preferred embodiments, the compositions are administered intravenously. See U.S. Pat. No. 7,498,298, at col. 152, lines 33-43.

Pharmaceutical compositions may be formulated such that the compounds of the invention are bioavailable upon administration to the patient. Compositions may take the form of one or more dosage units. For example, a tablet may be a single dosage unit, and a container of the compound of the invention in liquid form may hold a plurality of dosage units. See U.S. Pat. No. 7,498,298, at col. 152, lines 44-51.

The composition may be in the form of a liquid, e.g., a solution, emulsion or suspension. In a composition for administration by injection, the pharmaceutical composition includes one or more of a surfactant, preservative, wetting agent, dispersing agent, suspending agent, buffer, stabilizer and isotonic agent. See U.S. Pat. No. 7,498,298, at col. 153, lines 27-30.

Liquid pharmaceutical compositions may also include one or more of the following: sterile diluents such as water for injection, saline solution, preferably physiological saline, Ringer's solution, isotonic sodium chloride, fixed oils such as synthetic mono- or diglycerides, which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates, phosphates or amino acids; and agents for the adjustment of tonicity such as sodium chloride or dextrose. See U.S. Pat. No. 7,498,298, at col. 153, lines 31-43.

The amount of compound of formula (I) present in the pharmaceutical composition will depend on a variety of factors. Relevant factors include, without limitation, the type of patient (e.g., human), the particular form of compound, the manner of administration, and the composition employed.

Preferably, the compositions are formulated so that a dosage of between about 0.01 to about 20 mg/kg body weight/day of the compound of formula (I) can be administered to a patient receiving the composition. In some embodiments, the dosage administered to the patient is between about 0.01 mg/kg and about 10 mg/kg of the patient's body weight. In other embodiments, the dosage administered to the patient is between about 0.1 mg/kg and about 10 mg/kg of the patient's body weight. In yet another embodiment, the dosage administered to the patient is between about 0.1 mg/kg and about 5 mg/kg of the patient's body weight. In yet another embodiment, the dosage administered is between about 0.1 mg/kg and about 3 mg/kg of the patient's body weight. In yet another embodiment, the dosage administered is between about 1 mg/kg and about 3 mg/kg of the patient's body weight.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the nature and the severity of the particular disorder being treated. The amount of active ingredients will also depend upon the particular compound in the composition. The amount of active ingredient can be determined by standard clinical techniques. In addition, in vitro or in vivo assays can optionally be employed to help identify optimal dosage ranges.

The present invention also provides methods of using the compounds of formula (I) or pharmaceutical compositions thereof. The compounds and compositions are useful for killing or inhibiting the proliferation of tumor cells or cancer cells and for killing or inhibiting the replication of a cell that produces an autoimmune disease. The compounds and compositions are also useful for treating cancer, an autoimmune disease or an infectious disease in a patient.

In some embodiments, the present invention provides methods of killing or inhibiting the proliferation of tumor cells or cancer cells. In some embodiments, the method comprises contacting the tumor cells or cancer cells with a compound of the invention, or a pharmaceutically acceptable salt or solvate thereof, in an amount effective to kill or inhibit the proliferation of the tumor cells or cancer cells. In alternate embodiments, the method comprises contacting the tumor cells or cancer cells with a pharmaceutical composition comprising a compound of formula (I) in an amount effective to kill or inhibit the proliferation of the tumor cells or cancer cells.

The terms "cancer" and "cancerous" refer to the physiological condition or disorder in mammals characterized by unregulated cell growth. A "tumor" comprises one or more cancerous cells. See U.S. Pat. No. 7,498,298, at col. 29, lines 11-14.

Exemplary cancers include solid tumors, including but not limited to, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma; blood-borne cancers, including but not limited to: acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocytic leukemia, acute undifferentiated leukemia, chronic myelocytic leukemia (CML), chronic lymphocytic leukemia (CLL), hairy cell leukemia, multiple myeloma, acute and chronic leukemias: lymphoblastic, myelogenous, lymphocytic, myelocytic leukemias; lymphomas: Hodgkin's disease, non-Hodgkin's lymphoma, Waldenstrom's macroglobulinemia, heavy chain disease, polycythemia vera. In preferred embodiments, the cancer is selected from the group consisting of breast, ovarian, stomach, endometrial, salivary gland, lung, kidney, colon, colorectal, thyroid, pancreatic, prostate and bladder cancer. See U.S. Pat. No. 7,498,298, at cols. 157-158, Table 3.

In some embodiments, the method further comprises contacting the cells with an effective amount of a chemotherapeutic agent or a pharmaceutical composition thereof. The chemotherapeutic agent can be selected from the group consisting of a tubulin-forming inhibitor, a topoisomerase inhibitor, and a DNA binder.

The cells may be contacted with the compound of formula (I) and the chemotherapeutic agent simultaneously in either the same or different compositions or sequentially in any order. The amounts of compound of formula (I) and the chemotherapeutic agent and the relative timings of their contact will be selected in order to achieve the desired combined effect.

In another embodiment, the present invention provides a method for killing or inhibiting the replication of a cell that produces an autoimmune disease. In some embodiments, the method comprises comprising contacting the cell with a compound of formula (I), or a pharmaceutically acceptable salt or solvate thereof, in an amount effective to kill or inhibit the replication of the cell. In other embodiments, the method comprises contacting the cell with a pharmaceutical composition comprising a compound of formula (I) in an amount effective to kill or inhibit the replication of the cell.

In some embodiments, the cells are obtained from a patient having an autoimmune disease or from a relevant cell line.

Exemplary autoimmune diseases include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjogren's syndrome, Hashimoto's thyroiditis, Grave's disease, primary biliary cirrhosis, Wegener's granulomatosis, and tuberculosis); activated B lymphocyte-related disorders (e.g., systemic lupus erythematosus, Goodpasture's syndrome, rheumatoid arthritis, and type I diabetes); active chronic hepatitis, Addison's disease, allergic alveolitis, allergic reaction, allergic rhinitis, Alport's syndrome, anaphylaxis, ankylosing spondylitis, anti-phosholipid syndrome, arthritis, *ascariasis*, aspergillosis, atopic allergy, atropic aermatitis, atropic rhinitis, Behcet's disease, bird fancier's lung, bronchial asthma, Caplan's syndrome, cardiomyopathy, celiac disease, chagas' disease, chronic glomerulonephritis, Cogan's syndrome, cold agglutinin disease, congenital rubella infection, CREST syndrome, Crohn's disease, cryoglobulinemia, Cushing's syndrome, dermatomyositis, discoid lupus, Dressler's syndrome, echovirus infection, encephalomyelitis, endocrine opthalmopathy, Epstein-Barr virus infection, equine heaves, erythematosis, Evan's syndrome, Felty's syndrome, fibromyalgia, Fuch's cyclitis, gastric atrophy, gastrointestinal allergy, giant cell arteritis, glomerulonephritis, Goodpasture's syndrome, Guillain-Barre disease, hemolytic anemia, Henoch-Schonlein purpura, idiopathic adrenal atrophy, idiopathic pulmonary fibritis, IgA nephropathy, inflammatory bowel diseases, insulin-dependent diabetes mellitus, juvenile arthritis, juvenile diabetes mellitus (Type I), Lambert-Eaton syndrome, laminitis, lichen planus, lupoid hepatitis, lupus, lymphopenia, Meniere's disease, mixed connective tissue disease, multiple sclerosis, myasthenia gravis, pernicious anemia, polyglandular syndromes, presenile dementia, primary agammaglobulinemia, psoriasis, psoriatic arthritis, Raynauds phenomenon, recurrent abortion, Reiter's syndrome, rheumatic fever, Sampter's syndrome, schistosomiasis, Schmidt's syndrome, scleroderma, Shulman's syndrome, stiff-man syndrome, sympathetic ophthalmia, Takayasu's arteritis, temporal arteritis, thyroiditis, thrombocytopenia, thyrotoxicosis, toxic epidermal necrolysis, type B insulin resistance, type I diabetes mellitus, ulcerative colitis, uveitis, vitiligo, Waldenstrom's macroglobulemia.

In another embodiment, the present invention provides a method of determining inhibition of cellular proliferation by a compound of formula (I). The method comprises contacting cells in a cell culture medium with the compound of formula (I) and measuring the cytotoxic activity of the compound, whereby proliferation of the cells is inhibited. In some embodiments, the method further comprises culturing the cells for a period from about 6 hours to about 5 days.

Suitable cell lines are known to those skilled in the art and include those used for evaluating other auristatin drugs. Such cell lines include, but are not limited to, 786-O, a renal cell carcinoma; Caki-1, a renal cell carcinoma; L428, a Hodgkin's disease cell line; UMRC-3, a renal cell carcinoma; LP-1, a human myeloma cell line; and U251, a glioblastoma cell line.

In some embodiments, the cells are obtained from a patient having a disease to be treated (e.g., cancer, an autoimmune disease or an infectious disease) or from a relevant cell line.

In another embodiment, the present invention provides a method of measuring cell viability in the presence of a compound of formula (I). The method comprises contacting cells in a cell culture medium with the compound of formula (I), culturing the cells for a period from about 6 hours to about 5 days, preferably 96 hours; and measuring cell viability.

In some embodiments, the cells are obtained from a patient having a disease to be treated (e.g., cancer, an autoimmune disease or an infectious disease) or from a relevant cell line.

In another embodiment, the present invention provides a method for treating cancer in a patient. In some embodiments, the method comprises administering to the patient a compound of formula (I), or a pharmaceutically acceptable salt or solvate thereof, in an amount effective to treat cancer. In other embodiments, the method comprises administering to the patient a composition comprising a compound of formula (I) in an amount effective to treat cancer.

The terms "treat" or "treatment," unless otherwise indicated by context, refer to therapeutic treatment and prophylactic measures to prevent relapse and to inhibit or slow down (lessen) an undesired physiological change or disorder, such as the development or spread of cancer. For purposes of this invention, "treatment" includes, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already having the condition or disorder as well as those prone to have the condition or disorder. See U.S. Pat. No. 7,498,298, at col. 43, lines 13-29.

In the context of cancer, the term "treating" includes any or all of inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

The term "patient," as used herein, includes, but is not limited to, a human, rat, mouse, guinea pig, monkey, pig, goat, cow, horse, dog, cat, bird and fowl. In preferred embodiments, the patient is a human.

In some embodiments, the patient receives an additional treatment, such as radiation therapy, surgery, chemotherapy with another chemotherapeutic agent or combinations thereof. In some embodiments, the compound of the invention is administered concurrently with the chemotherapeutic agent or with radiation therapy or with surgery. In other embodiments, the chemotherapeutic agent or radiation therapy or surgery is administered or performed prior or subsequent to administration of a compound of the invention.

In some embodiments, the method for treating cancer further comprises administering to the patient an effective amount of a chemotherapeutic agent. Any one or a combination of the chemotherapeutic agents, such a standard of care chemotherapeutic agent(s), can be administered. In some embodiments, the chemotherapeutic agent may be selected from the group consisting of a tubulin-forming inhibitor, a topoisomerase inhibitor, and a DNA binder.

The compound of formula (I) and the chemotherapeutic agent may be administered simultaneously in either the same or different pharmaceutical composition or sequentially in any order. The amounts of compound of formula (I) and the chemotherapeutic agent and the relative timings of their administration will be selected in order to achieve the desired combined effect.

In another embodiment, the present invention provides a method of inhibiting the growth of tumor cells that overexpress a tumor-associated antigen in a patient. In some embodiments, the method comprises administering to the patient a compound of formula (I) conjugated to an antibody that is specific for said tumor-associated antigen, wherein the compound of formula (I) is administered in amount effective to inhibit growth of tumor cells in the patient. In alternate embodiments, the method comprises administering to the patient a pharmaceutical composition comprising a compound of formula (I) conjugated to an antibody that is specific for said tumor-associated antigen, wherein the compound of formula (I) is administered in amount effective to inhibit growth of tumor cells in the patient. The method may optionally further comprise administering to the patient a chemotherapeutic agent, or a pharmaceutical composition thereof, in an amount effective to inhibit the growth of tumor cells in the patient.

In some embodiments, the compound sensitizes the tumor cells to the chemotherapeutic agent.

In some embodiments, the compound induces cell death. In other embodiments, the compound induces apoptosis.

In some embodiments, the tumor cells are associated with a cancer selected from the group consisting of breast, ovarian, stomach, endometrial, salivary gland, lung, kidney, colon, colorectal, thyroid, pancreatic, prostate and bladder cancer.

In some embodiments, the compound of formula (I) is conjugated to an antibody selected from the group consisting of CD19, CD20, CD30, CD33, CD70, BCMA, Glypican-3, Liv-1 and Lewis Y.

In some embodiments, this method may be used to determine the efficacy and dosing of a compound of formula (I) or pharmaceutical compositions thereof. In such embodiments, the patient is an animal engineered to be, or is a model of, a disease involving the overexpression of a target protein to which the compound of formula (I) is conjugated. The animal is selected from the group consisting of a rat, mouse, guinea pig, monkey, pig, goat, cow, horse, dog, cat, bird and fowl.

For example, to test the efficacy in a renal xenograft model, 786-O (renal cell) xenografts are implanted subcutaneously into immunodeficient mice ($5 \times 10^6$ cells per mouse). Tumor volumes are calculated using the formula ($0.5 \times L \times W^2$) where L and W are the longer and shorter of two bidirectional measurements. Glioblastoma xenograft models are prepared using e.g., a DBTRGO5-MG glioblastoma subcutaneous model. DBTRGO5-MG cells are implanted subcutaneously into immunodeficient mice ($5 \times 10^6$ cells per mouse). Tumor volumes are calculated using the formula ($0.5 \times L \times W^2$) where L and W are the longer and shorter of two bidirectional measurements. In the same manner other tumor models can be generated and tested.

Tolerability of the compounds measured as maximum tolerated dose (MTD), is determined in mice based on animals' weight loss after treatment. Animals were usually monitored for 14 days. A compound is considered to be tolerated at a determined dose if single iv treatment at such dose results in a transient weight loss of no more than 20% of initial body weight of animals and no other signs of toxicity are observed.

In another embodiment, the present invention provides a method for treating an autoimmune disease in a patient. In some embodiments, the method comprises administering to the patient a compound of formula (I), or a pharmaceutically acceptable salt or solvate thereof, in an amount effective to treat the autoimmune disease. In other embodiments, the method comprises administering to the patient a pharmaceutical composition comprising a compound of formula (I) in an amount effective to treat the autoimmune disease.

In another embodiment, the present invention provides a method for treating an infectious disease in a patient. In some embodiments, the method comprises administering to the patient a compound of the invention, or a pharmaceutically acceptable salt or solvate thereof, in an amount effective to treat the infectious disease. In other embodiments, the method comprises administering to the patient a pharmaceutical composition comprising a compound of formula (I), in an amount effective to treat the infectious disease.

Examples of infectious diseases that may be treated by the compounds of formula (I) include, but are not limited to, bacterial diseases: diphtheria, pertussis, occult bacteremia, urinary tract infection, gastroenteritis, cellulitis, epiglottitis, tracheitis, adenoid hypertrophy, retropharyngeal abcess, impetigo, eethyma, pneumonia, endocarditis, septic arthritis, pneumococca, peritonitis, bactennia, meningitis, acute purulent meningitis, urethritis, cervicitis, proctitis, pharyngitis, salpingitis, epididymitis, gonorrhea, syphilis, listeriosis, anthrax, nocardiosis, *salmonella*, typhoid fever, dysentery, conjunctivitis, sinusitis, brucellosis, tullaremia, cholera, bubonic plague, tetanus, necrotizing enteritis, actinomycosis, mixed anaerobic infections, syphilis, relapsing fever, leptospirosis, lyme disease, rat bite fever, tuberculosis, lymphadenitis, leprosy, *chlamydia*, chlamydial pneumonia, trachoma, inclusion conjunctivitis; systemic fungal diseases: histoplamosis, coccidiodomycosis, blastomycosis, sporotrichosis, cryptococcsis, systemic candidiasis, aspergillosis, mucormycosis, mycetoma, *chromomycosis*; rickettsial diseases: typhus, Rocky Mountain spotted fever, ehrlichiosis, eastern tick-borne rickettsioses, rickettsialpox, Q fever, bartonellosis; parasitic diseases: malaria, babesiosis, African sleeping sickness, Chagas disease, leishmaniasis, dum-dum fever, toxoplasmosis, meningoencephalitis, keratitis, entamebiasis, giardiasis, cryptosporidiasis, isosporiasis, cyclosporiasis, microsporidiosis, *ascariasis*, whipworm infection, hookworm infection, threadworm infection, ocular larva migrans, trichinosis, Guinea worm disease, lymphatic filariasis, loiasis, river blindness, canine heartworm infection, schistosomiasis, swimmer's itch, oriental lung fluke, oriental liver fluke, fascioliasis, fasciolopsiasis, opisthorchiasis, tapeworm infections, hydatid disease, alveolar hydatid disease; viral diseases: measles, subacute sclerosing panencephalitis, common cold, mumps, rubella, roseola, fifth disease, chickenpox, respiratory syncytial virus infection, croup, bronchiolitis, infectious mononucleosis, poliomyelitis, herpangina, hand-foot-and-mouth disease, Bornholm disease, genital herpes, genital warts, aseptic meningitis, myocarditis, pericarditis, gastroenteritis, acquired immunodeficiency syndrome (AIDS), human immunodeficiency virus (HIV), Reye's syndrome, Kawasaki syndrome, influenza, bronchitis, viral "walking" pneumonia, acute febrile respiratory disease, acute pharyngoconjunctival fever, epidemic keratoconjunctivitis, herpes simplex virus 1 (HSV-1), herpes simplex virus 2 (HSV-2), shingles, cytomegalic inclusion disease, rabies, progressive multifocal leukoencephalopathy, kuru, fatal familial insomnia, Creutzfeldt-Jakob disease, Gerstmann-Straussler-Scheinker disease, tropical spastic paraparesis, western equine encephalitis, California encephalitis, St. Louis encephalitis, yellow fever, dengue, lymphocytic choriomeningitis, Lassa fever, hemorrhagic fever, hantavirus pulmonary syndrome, Marburg virus infections, Ebola virus infections, and smallpox.

Any compound or pharmaceutical composition described herein may be used in the methods of the present invention.

In some of the above methods, the compound of formula (I) is administered to a patient in a composition comprising a pharmaceutically acceptable carrier. In some of these embodiments, the composition is administered intravenously. In certain embodiments, the compound is formulated in a unit dosage injectable form.

In preferred embodiments of each of the above methods, the patient is a human.

In an additional embodiment, the present invention provides the use of a compound of formula (I) in the manufacture of a medicament for the treatment of any of the above mentioned cancers, autoimmune diseases or infectious diseases. It will be appreciated that a compound of formula (I) and one or more chemotherapeutic agents may be used in the manufacture of the medicament. The compound of formula (I) may be any of the compounds described above.

In additional embodiments, the present invention provides an article of manufacture comprising a compound of formula (I), a container, and a package insert or label indicating that the compound can be used to treat cancer characterized by the overexpression of at least one tumor-associated antigen. The compound of formula (I) may be any of the compounds described above.

The term "package insert" refers to instructions customarily included in commercial packages of therapeutic products, and containing information about the indication(s), usage, dosage, administration, contraindications and/or warnings concerning the use of such therapeutic products. See U.S. Pat. No. 7,498,298, at col. 34, lines 16-20.

In order that this invention be more fully understood, the following examples are set forth. These examples are for the purpose of illustration only and are not to be construed as limiting the scope of the invention in any way.

EXAMPLES

Example 1

General Experimental Procedures

N-Boc-Dolaproine and Dov-Val-Dil.TFA were synthesized as described earlier.[1,2] Reagents and anhydrous solvents were purchased from Acros Organics (Fisher Scientific), Sigma-Aldrich Chemical Company, and Lancaster Synthesis and were used as received. Diisopropylethylamine (DIEA) was redistilled over potassium hydroxide. Dibenzylphosphite was redistilled before use (bp 160° C. at 0.1 mm Hg). For thin-layer chromatography, Analtech silica gel GHLF Uniplates were used and visualized with short-wave UV irradiation and use of a permanganate dip followed by heating. Solvent extracts of aqueous solutions were dried over magnesium sulfate. For column chromatography, silica gel (230-400 mesh ASTM) from E. Merck (Darmstadt, Germany) was used. For ion-exchange chromatography, Dowex 50W×8-400 hydrogen form resin (Sigma-Aldrich) was washed with MeOH, hydrochloric acid (1 M), and deionized $H_2O$ before use. The cation forms of the resin were prepared by elution of an aqueous solution (1 M) of the corresponding base followed by deionized $H_2O$.

Melting points are uncorrected and were determined with a Fischer-Johns melting point apparatus. Optical rotations were measured by use of a Perkin-Elmer 241 polarimeter, and the $[\alpha]_D$ values are given in $10^{-1}$ deg $cm^2$ $g^{-1}$. The $^1H$, $^{13}C$ and $^{31}P$ NMR spectra were recorded using Varian Gemini 300 and Unity 400 and 500 instruments with deuterated solvents. The $^{31}P$ spectra were referenced to 80% phosphoric acid or to the corresponding $^1H$ spectra. High-resolution mass spectra were obtained with a Jeol JMS-LCmate mass spectrometer. Elemental analyses were determined by Galbraith Laboratories, Inc.

N-Boc-Dap-4-hydroxyphenethylamide (7a)

To a solution of Boc-Dap[1] (6, 0.49 g, 1.71 mmol) in dry DMF (3 mL) that was stirring at 20° C. was added 1-hydroxybenzotriazole (HOBT, 0.37 g, 2.74 mmol). Diisopropylethylamine (DIEA, 0.95 mL, 5.48 mmol) was added, followed by N-(3-dimethylaminopropyl)-N'-ethylcarbodiimide hydrochloride (EDCI), and the reaction mixture was stirred for 10 min before the addition of tyramine (0.28 g, 2.05 mmol). The mixture was stirred at 20° C. for 16 h before termination of reaction by addition of saturated NaHCO$_3$ solution (5 mL) and extraction with EtOAc (4×5 mL). The combined organic extract was washed with brine (20 mL) and dried. Removal of solvent yielded a yellow oil (0.89 g) that was fractionated by column chromatography (eluent: 2.5-6.0% CH$_3$OH in CH$_2$Cl$_2$) to provide 7a as a colorless oil (0.57 g, 82%) that crystallized from 1:1 CH$_2$Cl$_2$-hexane: mp 163-164° C.; $[\alpha]^{23}_D$ –30.4 (c 1.9, CHCl$_3$); IR (neat) $v_{max}$ 3305, 2975, 2935, 1650, 1515, 1168, 755 cm$^{-1}$; $^1$H NMR (CD$_3$OD, 300 MHz) δ 6.92 (d, J=8.4 Hz, 2H), 6.57 (d, J=8.4 Hz, 2H), 3.55 (br m, 1H), 3.49-3.33 (m, 3H), 3.29 (s, 3H), 3.26-3.19 (m, 2H), 3.19-3.03 (m, 2H), 2.70-2.53 (m, 2H), 2.11 (m, 1H), 1.81-1.70 (m, 2H), 1.61-1.50 (m, 2H), 1.40 (br s, 9H), 1.05 (d, J=6.3 Hz, 3H); $^{13}$C NMR (CDCl$_3$, 100.5 MHz) (two conformers observed) δ 174.7, 174.1, 155.5, 155.3, 154.8, 154.4, 129.5, 129.3, 115.5, 115.4, 83.7, 82.0, 80.1, 79.5, 60.6, 59.1, 58.6, 46.9, 46.5, 44.2, 43.8, 40.9, 40.7, 34.3, 28.5, 28.4, 25.7, 25.1, 24.4, 24.0, 14.3, 14.0; HRMS (FAB) m/z 407.2565 [M+H]$^+$ (calcd for C$_{22}$H$_{35}$N$_2$O$_5$, 407.2546).

Dap-4-hydroxyphenethylamide Hydrobromide (7b)

Bromotrimethylsilane (0.46 mL, 3.5 mmol) was added to a stirred solution of 7a (0.57 g, 1.4 mmol) in dry CH$_2$Cl$_2$ at 20° C., and stirring was continued for 18 h. Water (5 mL) was added, and the mixture was stirred vigorously for 30 min. The aqueous layer was removed, and the organic phase was extracted again with H$_2$O (5 mL). Freeze-drying of the combined aqueous phase provided the hydrobromide salt 7b as a colorless solid (0.54 g, 99%), which was used without further purification. A sample was crystallized from CH$_2$Cl$_2$-hexane: mp 79-81° C.; IR (neat) $v_{max}$ 3275, 2980, 1640, 1515, 1235, 830 cm$^{-1}$; $^1$H NMR (CD$_3$OD, 300 MHz) δ 6.95 (d, J=8.4 Hz, 2H), 6.60 (d, J=8.4 Hz, 2H), 3.47 (m, 1H), 3.41 (s, 3H), 3.25-3.02 (m, 5H), 2.72-2.62 (m, 2H), 2.33 (m, 1H), 1.88-1.76 (m, 2H), 1.72-1.64 (m, 2H), 1.13 (d, J=7.2 Hz, 3H); $^{13}$C NMR (CD$_3$OD, 125.5 MHz) δ 175.6, 157.0, 131.0, 130.8, 116.2, 81.6, 62.9, 61.8, 46.5, 45.5, 41.3, 35.2, 24.1, 23.9, 15.5; HRMS (APCI) m/z 307.2026 [(M–HBr)+H]$^+$ (calcd for C$_{17}$H$_{27}$N$_2$O$_3$, 307.2022).

Dov-Val-Dil-Dap-4-hydroxyphenethylamide (9)

To a solution of 8$^2$ (0.78 g, 1.43 mmol) that was stirring in dry DMF (2 mL) at 20° C. was added HOBT (0.31 g, 2.29 mmol). Next was added DIEA (0.96 mL, 5.50 mmol), followed by EDCI (0.44 g, 2.29 mmol), and the reaction mixture was stirred for 15 min before the addition of a solution of 7b (0.50 g, 1.30 mmol) in DMF (4 mL). The mixture was stirred at 20° C. for 6 h, and then reaction was terminated by addition of saturated NaHCO$_3$ solution (10 mL), followed by extraction of the mixture with EtOAc (4×10 mL). The combined organic extract was washed with brine (50 mL) and dried. Removal of solvent yielded a viscous brown oil (0.83 g) that was fractionated by column chromatography (eluent: 5-10% MeOH in CH$_2$Cl$_2$) to provide 9 as a viscous colorless oil (0.61 g, 65%): $[\alpha]^{23}_D$ –44.0 (c 2.2, CHCl$_3$); IR (neat) $v_{max}$ 3295, 2965, 1620, 1515, 1100, 755 cm$^{-1}$; $^1$H NMR (CD$_3$OD, 400 MHz) δ 7.25 (m, 1H), 7.05-7.01 (m, 4H), 6.68 (t, J=8.5 Hz, 4H), 4.74 (d, J=8.4 Hz, 1H), 4.71 (d, J=8.4 Hz, 1H), 4.63 (d, J=8.8 Hz, 1H), 4.15 (m, 1H), 4.07 (m, 1H), 3.90-3.83 (m, 2H), 3.78 (m, 1H), 3.68 (m, 1H), 3.57 (m, 6H), 3.40-3.32 (m, 2H), 3.38 (s, 3H), 3.36 (s, 3H), 3.29 (s, 6H), 3.26 (s, 3H), 3.13 (s, 3H), 2.81-2.68 (m, 4H), 2.65-2.62 (m, 2H), 2.48 (d, J=6.6 Hz, 2H), 2.31 (s, 6H), 2.29 (s, 6H), 2.27-2.19 (m, 2H), 2.08-1.86 (m, 10H), 1.78-1.63 (m, 4H), 1.44-1.35 (m, 2H), 1.16 (t, J=7.1 Hz, 6H), 1.05-0.95 (m, 28H), 0.90-0.84 (m, 12H); $^{13}$C NMR (CD$_3$OD, 100.5 MHz) δ 176.5, 176.4, 175.3, 173.3, 173.2, 171.9, 157.0, 156.9, 136.5, 131.2, 130.9, 130.8, 130.7, 116.3, 116.2, 87.2, 83.6, 79.8, 76.0, 75.8, 62.1, 61.4, 61.0, 60.8, 58.6, 58.3, 57.8, 56.2, 56.0, 45.9, 45.7, 42.5, 42.4, 41.8, 41.4, 38.2, 35.3, 33.8, 33.1, 31.8, 31.7, 28.8, 27.0, 26.8, 25.8, 24.5, 20.2, 20.2, 19.9, 19.5, 19.3, 16.3, 16.0, 15.8, 15.1, 10.9, 10.8; HRMS (FAB) m/z 718.5084 [M+H]$^+$ (calcd for C$_{39}$H$_{68}$N$_5$O$_7$, 718.5119).

Dov-Val-Dil-Dap-4-(dibenzylphosphoryloxy)phenethylamide (10a)

To a solution of 9 (0.51 g, 0.70 mmol) in dry CH$_3$CN (4 mL) at –15° C. (ice/salt) was added carbon tetrachloride (0.34 mL, 1.02 mmol), followed by DIEA (0.26 mL, 1.50 mmol) and 4-dimethylaminopyridine (9 mg, 0.07 mmol). Dibenzylphosphite (0.23 mL, 1.02 mmol) was next added over a 20-min period to the mixture, the temperature being maintained between –15 and –18° C. After addition, the mixture was cooled to –20° C. and then allowed to warm to 5° C. over 90 min, and reaction was terminated by addition of saturated NaHCO$_3$ solution (10 mL). The mixture was extracted with EtOAc (3×10 mL), and the combined organic extract was washed with brine (50 mL) and dried. Removal of solvent yielded a viscous pale yellow oil (0.60 g) that was fractionated by column chromatography (eluent: 5-10% MeOH in CH$_2$Cl$_2$) to provide 10a as a colorless oil (0.34 g, 49%): IR (neat) $v_{max}$ 3305, 2965, 1620, 1455, 1215, 1015, 955 cm$^{-1}$; $^1$H NMR (CD$_3$OD, 500 MHz) δ 7.36-7.31 (m, 20H), 7.21 (d, J=6.6 Hz, 2H), 7.20 (d, J=6.6 Hz, 2H), 7.07 (d, J=6.6 Hz, 2H), 7.03 (d, J=6.6 Hz, 2H), 5.13-5.10 (m, 8H), 4.81-4.71 (m, 2H), 4.71 (d, J=8.0 Hz, 1H), 4.62 (d, J=8.0 Hz, 1H), 4.14 (m, 1H), 4.06 (m, 1H), 3.91-3.86 (m, 2H), 3.80 (m, 1H), 3.69 (m, 1H), 3.56-3.47 (m, 4H), 3.43-3.32 (m, 2H), 3.38 (s, 3H), 3.36 (s, 3H), 3.28 (s, 6H), 3.26 (s, 3H), 3.11 (s, 3H), 2.86-2.77 (m, 4H), 2.65-2.61 (m, 3H), 2.51 (m, 1H), 2.46 (d, J=6.5 Hz, 2H), 2.30 (s, 6H), 2.29 (s, 6H), 2.28-2.18 (m, 2H), 2.08-1.86 (m, 9H), 1.76-1.64 (m, 5H), 1.43-1.36 (m, 2H), 1.16 (d, J=7.5 Hz, 3H), 1.15 (d, J=7.5 Hz, 3H), 1.02-0.92 (m, 28H), 0.87-0.81 (m, 12H); $^{13}$C NMR (CD$_3$OD, 125.5 MHz) δ 175.2, 175.1, 171.9, 170.6, 157.0, 149.0 (d, J$_{C-P}$=7.0 Hz), 148.9 (d, J$_{C-P}$=7.0 Hz), 136.6, 136.4, 129.9, 129.8, 128.5, 128.3, 127.9 (d, J$_{C-P}$=2.6 Hz), 119.8 (d, J$_{C-P}$=4.4 Hz), 119.6 (d, J$_{C-P}$=4.4 Hz), 85.7, 82.2, 78.5, 78.4, 74.5, 74.4, 70.1, 70.1, 60.7, 60.0, 59.6, 57.3, 56.9, 54.8, 54.6, 46.7, 44.5, 44.3, 41.1, 41.1, 40.0, 39.7, 36.8, 35.6, 34.1, 32.3, 32.2, 31.7, 30.4, 30.3, 27.4, 25.7, 25.5, 24.4 (d, J$_{C-P}$=3.6 Hz), 23.1, 18.8 (d, J$_{C-P}$=4.4 Hz), 18.5, 18.2, 18.0, 14.9, 14.6, 14.5, 13.7, 9.5; $^{31}$P NMR (CD$_3$OD, 202.5 MHz) δ –6.51, –6.54; HRMS (FAB) m/z 978.5811 [M+H]$^+$ (calcd for C$_{53}$H$_{81}$N$_5$O$_{10}$P 978.5721).

Dov-Val-Dil-Dap-4-(dihydrophosphoryloxy)phenethylamide (10b)

To a solution of dibenzyl phosphate 10a (38 mg, 0.04 mmol) in MeOH (5 mL) was added palladium on activated carbon (10 wt % Pd, 10 mg), and hydrogen gas (balloon) was bubbled through the suspension for 1 h. The mixture was filtered through a plug of Celite, and the filter was washed with MeOH (2×5 mL). Removal of solvent from the filtrate yielded the free phosphoric acid 10b as a glassy solid (32 mg, quantitative): mp 168-170° C.; IR (neat) $v_{max}$ 3400, 2970, 1635, 1460, 1095, 910 cm$^{-1}$; $^1$H NMR (CD$_3$OD, 500 MHz) δ 7.20-7.12 (m, 8H), 4.77-4.71 (m, 2H), 4.67 (d, J=8.5 Hz, 1H), 4.62 (d, J=9.0 Hz, 1H), 4.11 (m, 1H), 4.05 (m, 1H), 3.93-3.89

(m, 2H), 3.73-3.68 (m, 2H), 3.61-3.48 (m, 4H), 3.44-3.33 (m, 2H), 3.41 (s, 3H), 3.37 (s, 3H), 3.29 (s, 6H), 3.28 (s, 3H), 3.15 (s, 3H), 2.90 (s, 6H), 2.79-2.73 (m, 4H), 2.66-2.49 (m, 4H), 2.42-2.26 (m, 4H), 2.08-1.64 (m, 14H), 1.46-1.38 (m, 2H), 1.23 (d, J=7.0 Hz, 3H), 1.17 (d, J=7.0 Hz, 3H), 1.07-1.00 (m, 20H), 0.97-0.84 (m, 20H); $^{31}$P NMR (CD$_3$OD, 202.5 MHz) δ −4.11.

Sodium Auristatin TP (3b)

Ion-exchange chromatography of free acid 10b (32 mg) with aqueous NaOH led to 3b as a colorless solid (24 mg, 71%): mp 170-171° C.; IR (neat) $v_{max}$ 3305, 2965, 1625, 1510, 1105, 990 cm$^{-1}$; $^1$H NMR (CD$_3$OD, 400 MHz) δ 7.17-7.15 (m, 4H), 7.09 (d, J=8.0 Hz, 4H), 4.78-4.72 (m, 2H), 4.72 (d, J=8.0 Hz, 1H), 4.64 (d, J=8.4 Hz, 1H), 4.12 (m, 1H), 4.07 (m, 1H), 3.98-3.94 (m, 2H), 3.91 (dd, J=9.1, 2.3 Hz, 2H), 3.70 (m, 1H), 3.59 (m, 1H), 3.51-3.41 (m, 4H), 3.39 (s, 3H), 3.37 (s, 3H), 3.36-3.32 (m, 2H), 3.30 (s, 6H), 3.27 (s, 3H), 3.14 (s, 3H), 2.81-2.70 (m, 4H), 2.65 (d, J=7.2 Hz, 1H), 2.63 (d, J=7.2 Hz, 1H), 2.49 (d, J=6.4 Hz, 2H), 2.31 (s, 6H), 2.29 (s, 6H), 2.29-2.22 (m, 2H), 2.08-1.87 (m, 9H), 1.81-1.68 (m, 5H), 1.43-1.36 (m, 2H), 1.17 (t, J=5.3 Hz, 6H), 1.03-0.95 (m, 28H), 0.85 (q, J=7.2 Hz, 12H); $^{31}$P NMR (CD$_3$OD, 162.0 MHz) δ −3.42.

Lithium Auristatin TP (3a)

Ion-exchange chromatography of sodium salt 3b (12 mg, 0.014 mmol) with aqueous LiOH led to 3a as a colorless solid (11 mg, 96%): mp 263° C. (dec); IR (neat) $v_{max}$ 3315, 2965, 1630, 1105, 1005, 920 cm$^{-1}$; $^1$H NMR (CD$_3$OD, 400 MHz) δ 7.20 (d, J=8.0 Hz, 2H), 7.18 (d, J=8.0 Hz, 2H), 7.04 (d, J=8.0 Hz, 4H), 4.74-4.70 (m, 2H), 4.72 (d, J=8.0 Hz, 1H), 4.64 (d, J=8.8 Hz, 1H), 4.14-4.00 (m, 4H), 3.95 (m, 1H), 3.91 (dd, J=9.0, 2.2 Hz, 1H), 3.71 (m, 1H), 3.58 (m, 1H), 3.52-3.34 (m, 6H), 3.39 (s, 3H), 3.38 (s, 3H), 3.30 (s, 6H), 3.27 (s, 6H), 3.13 (s, 3H), 2.75-2.68 (m, 4H), 2.64 (d, J=4.8 Hz, 1H), 2.63 (d, J=4.8 Hz, 1H), 2.51 (d, J=6.4 Hz, 2H), 2.30 (s, 6H), 2.29 (s, 6H), 2.27-2.23 (m, 2H), 2.07-1.94 (m, 9H), 1.82-1.71 (m, 5H), 1.45-1.37 (m, 2H), 1.18 (t, J=6.2 Hz, 6H), 1.03-0.95 (m, 28H), 0.85 (q, J=6.9 Hz, 12H); $^{31}$P NMR (CD$_3$OD, 162.0 MHz) δ −0.58.

Potassium Auristatin TP (3c)

Ion-exchange chromatography of acid 10b with aqueous KOH led to 3c as a colorless solid (4 mg, 64%): mp 198° C.; IR (neat) $v_{max}$ 3230, 2965, 1620, 1100, 980, 885 cm$^{-1}$; $^1$H NMR (CD$_3$OD, 400 MHz) δ 7.21 (d, J=8.2 Hz, 2H), 7.19 (d, J=8.2 Hz, 2H), 7.04 (d, J=8.2 Hz, 4H), 4.75-4.72 (m, 2H), 4.72 (d, J=8.0 Hz, 1H), 4.64 (d, J=6.6 Hz, 1H), 4.14-4.01 (m, 4H), 3.95 (m, 1H), 3.91 (dd, J=8.8, 2.4 Hz, 1H), 3.71 (m, 1H), 3.58 (m, 1H), 3.52-3.35 (m, 6H), 3.39 (s, 3H), 3.38 (s, 3H), 3.30 (s, 6H), 3.26 (s, 3H), 3.13 (s, 3H), 2.75-2.68 (m, 4H), 2.64 (d, J=8.8 Hz, 1H), 2.63 (d, J=9.2 Hz, 1H), 2.49 (d, J=5.6 Hz, 2H), 2.30 (s, 6H), 2.29 (s, 6H), 2.27-2.23 (m, 2H), 2.07-1.94 (m, 9H), 1.83-1.72 (m, 5H), 1.45-1.37 (m, 2H), 1.18 (t, J=6.2 Hz, 6H), 1.03-0.95 (m, 28H), 0.84 (q, J=6.9 Hz, 12H); $^{31}$P NMR (CD$_3$OD, 162.0 MHz) δ −0.42.

Morpholine Auristatin TP (3d)

Ion-exchange chromatography of potassium salt 3c with aqueous morpholine led to 3d as a colorless solid: mp 148-150° C.; IR (neat) $v_{max}$ 3295, 2965, 1620, 1455, 1105, 880 cm$^{-1}$; $^1$H NMR (CD$_3$OD, 500 MHz) δ 7.18-7.11 (m, 8H), 4.82-4.74 (m, 2H), 4.71 (d, J=8.5 Hz, 1H), 4.65 (d, J=8.5 Hz, 1H), 4.13 (m, 1H), 4.07 (m, 1H), 3.97 (m, 1H), 3.91 (dd, J=9.3, 2.3 Hz, 1H), 3.80 (br s, 16H), 3.71 (m, 1H), 3.60 (m, 1H), 3.52 (d, J=8.5 Hz, 1H), 3.49-3.43 (m, 3H), 3.40 (s, 3H), 3.39 (s, 3H), 3.37-3.34 (m, 2H), 3.31 (s, 6H), 3.28 (s, 3H), 3.15 (s, 3H), 3.06 (br s, 16H), 2.82 (m, 1H), 2.77 (q, J=7.2 Hz, 4H), 2.69 (d, J=8.5 Hz, 1H), 2.67 (m, 1H), 2.54 (d, J=9.0 Hz, 1H), 2.50 (d, J=6.0 Hz, 2H), 2.42 (s, 6H), 2.34 (s, 6H), 2.32-2.14 (m, 2H), 2.13-1.88 (m, 9H), 1.81-1.71 (m, 5H), 1.46-1.38 (m, 2H), 1.20 (d, J=6.5 Hz, 3H), 1.18 (d, J=7.5 Hz, 3H), 1.04-0.95 (m, 28H), 0.91-0.87 (m, 12H); $^{31}$P NMR (CD$_3$OD, 162.0 MHz) δ −3.43.

General Procedure for the Synthesis of 3e-h

The amine or amino acid (25.0 μmol) was added to a stirred solution of acid 10b (10 mg, 12.5 μmol) in either MeOH (300 μL) or deionized H$_2$O (for 3 h), and the mixture was stirred for 15 h. Removal of solvent yielded the desired salt.

Quinine Auristatin TP (3e)

colorless solid; mp 118-120° C.; $^1$H NMR (CD$_3$OD, 500 MHz) δ 8.67 (d, J=4.8 Hz, 4H), 7.93 (d, J=9.3 Hz, 4H), 7.72 (d, J=4.8 Hz, 4H), 7.43 (d, J=2.3 Hz, 4H), 7.40 (dd, J=9.3, 2.3 Hz, 4H), 7.17 (t, J=7.3 Hz, 4H), 7.03 (d, J=7.3 Hz, 4H), 5.93 (s, 4H), 5.73 (m, 4H), 5.05 (d, J=17.5 Hz, 4H), 4.95 (d, J=11 Hz, 4H), 4.82-4.71 (m, 2H), 4.72 (d, J=8.0 Hz, 1H), 4.65 (d, J=8.5 Hz, 1H), 4.12 (m, 1H), 4.07 (m, 1H), 3.98 (s, 12H), 3.91 (d, J=2.0 Hz, 1H), 3.89 (d, J=2.0 Hz, 1H), 3.71-3.65 (m, 2H), 3.56 (m, 1H), 3.50 (d, J=10.0 Hz, 1H), 3.45-3.23 (m, 12H), 3.39 (s, 3H), 3.38 (s, 3H), 3.30 (s, 3H), 3.29 (s, 3H), 3.27 (s, 3H), 3.14 (s, 3H), 3.00-2.92 (m, 8H), 2.71-2.65 (m, 6H), 2.56-2.48 (m, 8H), 2.34 (s, 6H), 2.31 (s, 6H), 2.30-2.21 (m, 2H), 2.08-1.90 (m, 24H), 1.78-1.71 (m, 10H), 1.45-1.40 (m, 6H), 1.17 (t, J=7.0 Hz, 6H), 1.04-0.95 (m, 28H), 0.98-0.80 (m, 12H); $^{31}$P NMR (CD$_3$OD, 162.0 MHz) δ −1.82.

TRIS Auristatin TP (3f)

colorless solid; mp 122-123° C.; $^1$H NMR (D$_2$O, 500 MHz) δ 7.21-7.12 (m, 1H), 4.73-4.64 (m, 4H), 4.17 (m, 1H), 4.11 (m, 1H), 3.92-3.86 (m, 2H), 3.74-3.62 (m, 2H), 3.67 (s, 24H), 3.59-3.38 (m, 6H), 3.44 (s, 3H), 3.42 (s, 3H), 3.33 (s, 3H), 3.33 (s, 3H), 3.26 (s, 3H), 3.18 (s, 3H), 3.12 (d, J=8.5 Hz, 3H), 3.02 (d, J=9.5 Hz, 1H), 2.87-2.75 (m, 2H), 2.67-2.62 (m, 2H), 2.58-2.54 (m, 2H), 2.52 (s, 6H), 2.45 (s, 6H), 2.36-2.27 (m, 2H), 2.22-2.09 (m, 2H), 2.08-2.01 (m, 2H), 1.99-1.72 (m, 9H), 1.68-1.61 (m, 1H), 1.39-1.30 (m, 2H), 1.20 (d, J=6.5 Hz, 3H), 1.16 (d, J=7.0 Hz, 3H), 1.05-0.97 (m, 28H), 0.88-0.84 (m, 12H); $^{31}$P NMR (CD$_3$OD, 162.0 MHz) δ −0.01.

Serine Auristatin TP (3g)

colorless solid; mp 158° C. (dec); $^1$H NMR (D$_2$O, 500 MHz) δ 7.26 (d, J=8.5 Hz, 2H), 7.23 (d, J=8.5 Hz, 2H), 7.14 (d, J=8.5 Hz, 2H), 7.09 (d, J=8.5 Hz, 2H), 4.75 (d, J=9.5 Hz, 1H), 4.73-4.68 (m, 2H), 4.66 (d, J=9.5 Hz, 1H), 4.18 (m, 1H), 4.11 (m, 1H), 4.01-3.93 (m, 10H), 3.86-3.83 (m, 6H), 3.79 (t, J=5.8 Hz, 2H), 3.74-3.68 (m, 2H), 3.62-3.51 (m, 4H), 3.47-3.36 (m, 4H), 3.44 (s, 3H), 3.39 (s, 3H), 3.33 (s, 3H), 3.32 (s, 3H), 3.24 (s, 3H), 3.18 (s, 3H), 2.97 (s, 6H), 2.95 (s, 6H), 2.92-2.79 (m, 4H), 2.67-2.44 (m, 6H), 2.33 (m, 1H), 2.24 (m, 1H), 2.12-2.02 (m, 2H), 1.97-1.66 (m, 9H), 1.51 (m, 1H), 1.38-1.32 (m, 2H), 1.20 (d, J=7.0 Hz, 3H), 1.14 (d, J=7.0 Hz, 3H), 1.05-0.95 (m, 30H), 0.92-0.82 (m, 10H); $^{31}$P NMR (CD$_3$OD, 162.0 MHz) δ −4.07.

Nitroarginine Auristatin TP (3h)

colorless solid; mp 157-158° C. (dec); IR (neat) $v_{max}$ 3295, 2965, 1625, 1360, 1270, 1095 cm$^{-1}$; $^1$H NMR (D$_2$O, 500 MHz) δ 7.21 (d, J=7.8 Hz, 2H), 7.18 (d, J=7.8 Hz, 2H), 7.10 (d, J=7.8 Hz, 2H), 7.05 (d, J=7.8 Hz, 2H), 4.71 (d, J=9.0 Hz, 1H), 4.70-4.64 (m, 2H), 4.62 (d, J=8.5 Hz, 1H), 4.14 (m, 1H), 4.06 (m, 1H), 3.81-3.72 (m, 4H), 3.74 (t, J=6.5 Hz, 4H), 3.69-3.63 (m, 2H), 3.59-3.45 (m, 4H), 3.43-3.33 (m, 2H), 3.40 (s, 3H), 3.35 (s, 3H), 3.30 (t, J=6.5 Hz, 8H), 3.29 (s, 3H), 3.28 (s, 3H), 3.20 (s, 3H), 3.14 (s, 3H), 2.93 (s, 6H), 2.90 (s, 6H), 2.88-2.75 (m, 4H), 2.63-2.48 (m, 5H), 2.44-2.39 (m, 1H), 2.29 (m, 1H), 2.20 (m, 1H), 2.08-1.97 (m, 2H), 1.95-1.61 (m, 25H), 1.47 (m, 1H), 1.34-1.27 (m, 2H), 1.16 (d, J=6.5 Hz, 3H), 1.10 (d, J=7.0 Hz, 3H), 1.01-0.96 (m, 18H), 0.93-0.90 (m, 12H), 0.86-0.81 (m, 10H); $^{31}$P NMR (CD$_3$OD, 162.0 MHz) δ −3.56.

N-Boc-Dap-2-aminoquinoline (11)

To a solution of Boc-Dap$^1$ (6, 0.172 g; 0.6 mmol) in CH$_2$Cl$_2$ (3 mL) was added 2-aminoquinoline (82.8 mg; 0.57 mmol), and the mixture was stirred and cooled to 0° C. under argon. Triethylamine (TEA, 0.3 mL; 2.1 mmol) and diethylcyanophosphonate (DEPC; 0.2 mL; 1.2 mmol) were added, and the resultant yellow solution was allowed to warm to room temperature (rt) and was stirred under argon for 6 h. Removal of solvent yielded a dark orange-brown residue that was fractioned under pressure on silica gel [eluent: hexane-acetone (7:2 to 2:3)] to give the product as a colorless solid (90.8 mg, 0.22 mmol, 36.6%, based on recovery of starting material): $^1$H NMR (CDCl$_3$, 300 MHz) δ 8.43 (1H, dd, J=8.7, 1.5 Hz), 8.16 (1H, d, J=8.7 Hz), 7.83 (1H, d, J=8.7 Hz), 7.72 (1H, d, J=8.4 Hz), 7.66 (1H, t, J=7.5 Hz), 7.44 (1H, t, J=7.5 Hz), 4.05-3.92 (2H, m, NCH, OCH), 3.53 (3H, s, OCH$_3$), 3.44 (2H, br d, J=13 Hz, NCH$_2$), 2.60-2.80 (1H, m, CHCH$_3$), 1.74-1.98 (4H, m, 2×CH$_2$), 1.52 (9H, s, C(CH$_3$)$_3$), 1.45 (3H, d, J=9.3 Hz, CHCH$_3$)); MS (APCI+) m/z 414.2373 [M+H]$^+$ (calcd for C$_{23}$H$_{32}$N$_3$O$_4$, 414.2393).

Dap-2-aminoquinoline Trifluoroacetate (12)

To a solution of N-Boc-Dap-2-AQ (11, 68.0 mg, 0.16 mmol) in CH$_2$Cl$_2$ (4 mL) that was stirring at 0° C. under argon was added trifluoroacetic acid (TFA, 2 mL), and stirring was continued for 2 h with warming to rt. The solvent was removed under vacuum, toluene being used to form an azeotrope with the remaining TFA. The residue, a yellow oil, was allowed to stand under diethyl ether for 1 h. Removal of the ether left a yellowish oily solid to which hexane was added and removed under vacuum until a constant weight was reached (99.4 mg; quantitative), and this material was used immediately in the next reaction.

Dov-Val-Dil-Dap-2-aminoquinoline (Auristatin 2-AQ, 4)

The Dap-2-AQ salt 12 and Dov-Val-Dil.TFA$^2$ (8, 87.0 mg; 0.16 mmol) were dissolved in CH$_2$Cl$_2$ (5 mL), and the solution was stirred under argon and cooled to 0° C. Next, TEA (0.12 mL; 0.86 mmol) and DEPC (0.035 mL; 0.21 mmol) were added, and the mixture was stirred under argon for 7 h with warming to rt. Removal of solvent yielded a yellowish oil (310 mg) that was separated on silica gel under pressure [eluent: hexane-acetone (5:2 to 3:2)] to give the product as a colorless glass (powder when scratched) (64 mg; 0.09 mmol): $^1$H NMR (CDCl$_3$, 300 MHz) δ 8.43 (1H, dd, J=8.7, 1.5 Hz), 8.14 (1H, d, J=8.7 Hz), 7.80-7.41 (4H, m), 6.90 (1H, t, J=9.3 Hz), 6.73 (1H, d, J=9.0 Hz), 4.86 (1H, m), 4.75 (1H, m), 4.26 (1H, m), 4.14 (1H, m), 4.04 (1H, m), 3.51 and 3.44 (3H, s), 3.35 and 3.32 (3H, s), 3.38-3.19 (2H, m), 3.02 (3H, s), 2.42 (3H, m), 2.23 (6H, s), 2.23 (1H, m), 2.08-1.98 (5H, m), 1.95-1.74 (1H, m), 1.43-1.33 (2H, m), 0.80-1.06 (22H, m); MS (APCI+) m/z 725.4997 [M+H]$^+$ (calcd for C$_{40}$H$_{65}$N$_6$O$_6$, 725.4966).

N-Boc-Dap-6-aminoquinoline (14)

Method A:

To a stirring solution of Boc-Dap$^1$ (6, 87.2 mg; 0.3 mmol) in DMF (2 mL) and pyridine (0.1 mL) was added Boc$_2$O (0.183 g; 0.84 mmol). After 10 min, 6-aminoquinoline (6-AQ; 50.4 mg; 0.35 mmol) was added to the solution, and stirring was continued for 64 h, at which time starting material was still present. Solvent was removed from the mixture, and the residue was fractionated by column chromatography in hexane-acetone (5:1 to 2:1 gradient). The first fractions to elute contained Boc-6-AQ (35 mg): $^1$H NMR (CDCl$_3$, 300 MHz) δ 8.79 (1H, dd, J=4.5, 1.5 Hz), 8.01-8.12 (3H, m), 7.48 (1H, dd, J=9, 2.7 Hz), 7.36 (1H, dd, J=7.1, 4.2 Hz), 7.03 (1H, br s), 1.55 (9H, s).

Following the elution of the remaining Boc-Dap (6), compound 14 (29.7 mg, 0.07 mmol, 23% yield, or 28% based on 14.9-mg recovery of 6-AQ) was collected: $^1$H NMR (CDCl$_3$, 300 MHz) δ 8.82 (2H, m), 8.45 (1H, br s), 8.11 (1H, d, J=8.1 Hz), 8.04 (1H, d, J=9.3 Hz), 7.72 (1H, br), 7.37 (1H, dd, J=8.4, 4.2 Hz), 4.15-3.90 (2H, m, NCH, OCH), 3.55 (3H, s, OCH$_3$), 3.43 (m, 1H), 3.27 (m, 1H), 2.72 (1H, m), 2.06-1.76 (4H, m), 1.50 (9H, s), 1.39 (3H, m); MS (APCI+) m/z 414.2408 [M+H]$^+$ (calcd for C$_{23}$H$_{32}$N$_3$O$_4$, 414.2393).

Method B:

Intermediate acid fluoride 16 was first prepared by successive addition of pyridine (0.05 mL) and cyanuric fluoride (15, 0.15 mL, 1.75 mmol) to a solution of Boc-Dap (6, 76.3 mg, 0.27 mmol) that was stirring under argon at 0° C., with continued stirring for 20 h and warming to rt. Next, CH$_2$Cl$_2$ (10 mL) and ice were added, followed by cold H$_2$O. The organic phase was removed and the aqueous layer was further extracted with CH$_2$Cl$_2$. The combined organic extract was washed with cold H$_2$O and dried to give a dark orange oily solid (65.6 mg) that by tlc comprised product 16 and a trace of Boc-Dap (6). Without further purification, the crude product was dissolved in CH$_2$Cl$_2$ and was treated with pyridine (0.1 mL) followed by 6-AQ (34.8 mg, 0.24 mmol). The mixture was stirred for 21 h and was then extracted with CH$_2$Cl$_2$ (10 mL). The solution was washed with 10% citric acid solution, followed by H$_2$O. Drying over Na$_2$SO$_4$ and removal of solvent yielded a pale brown oil (52.8 mg) that was separated by column chromatography [eluent: toluene-acetone (2:1)] to give product 14 (30.3 mg, 0.07 mmol, 26%).

Dap-6-aminoquinoline Trifluoroacetate (17)

To a solution of N-Boc-Dap-6-AQ (14, 49.3 mg, 0.12 mmol) in CH$_2$Cl$_2$ (2 mL) that was stirring at 0° C. under argon was added trifluoroacetic acid (TFA, 2 mL). Stirring was continued for 3 h with warming to rt. The solvent was removed under vacuum, toluene being used to form an azeotrope with the remaining TFA, to give a green-tinged oily solid (17; quantitative) that was used immediately in the next reaction.

Dov-Val-Dil-Dap-6-aminoquinoline (Auristatin 6-AQ, 5)

Dap-6-AQ salt 17 (0.12 mmol) and Dov-Val-Dil.TFA² (8, 70.0 mg; 0.13 mmol) were dissolved in CH₂Cl₂ (2 mL), and the solution was stirred under argon and cooled to 0° C. Next were added TEA (0.11 mL; 0.79 mmol) and DEPC (0.03 mL; 0.18 mmol), and the mixture was stirred under argon for 18 h with warming to rt. Removal of solvent and separation on silica gel under pressure [eluent: hexane-acetone (5:2 to 2:3)] gave the crude product 5 (48.6 mg), of which a 19.1-mg sample was further purified by column chromatography in CH₂Cl₂-MeOH (19:1) to give auristatin 6-AQ (5) as a pale yellow glassy oil (powder when scratched): ¹H NMR (CDCl₃, 300 MHz) δ 9.04 (1H, br s), 8.81 (1H, br d, J=3 Hz), 8.47 (1H, s), 8.11 (1H, d, J=8.4 Hz), 8.02 (1H, d, J=9.3 Hz), 7.76 (1H, br d, J=8.7 Hz), 7.36 (1H, dd, J=8.4, 3.8 Hz), 6.96 (1H, br), 4.79 (2H, m), 4.30-4.07 (3H, m), 3.51 (3H, s), 3.50-3.26 (2H, m), 3.35 (3H, s), 3.05 (s, 3H), 2.71 (1H, m), 2.54-2.42 (2H, m), 2.32-2.22 (1H, m), 2.28 (6H, s), 2.12-2.05 (2H, m), 1.82 (2H, m), 1.42-1.26 (5H, m), 1.08-0.80 (21H, m); MS (APCI+) m/z 725.4907 [M+H]⁺ (calcd for C₄₀H₆₅N₆O₆, 725.4966).

Example 2

Results and Discussion

The synthesis of 3 was carried out as shown in Scheme 1. Reaction of the γ-amino acid Boc-Dap (6)¹ with tyramine in the presence of 1-(3-dimethylaminopropyl)-3-ethylcarbodiimide hydrochloride (EDCl) and 1-hydroxybenzotriazole (HOBT) gave the protected amide 7a. Removal of the Boc group with bromotrimethylsilane (TMSBr) yielded the hydrobromide salt (7b), which was coupled with Dov-Val-Dil.TFA (8)² in the presence of EDCl and HOBT to give the parent auristatin tyramide (9). The doubling of signals in the ¹H and ¹³C NMR spectra of 9 indicated the presence of two isomers, a pattern similar to that of dolastatin 10 and due to conformational isomers arising from cis-trans isomerism at the Dil-Dap bond.²

SCHEME 1

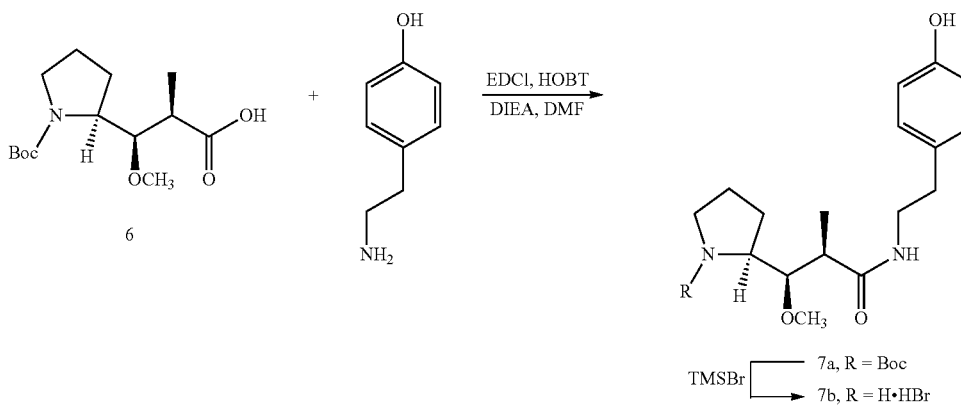

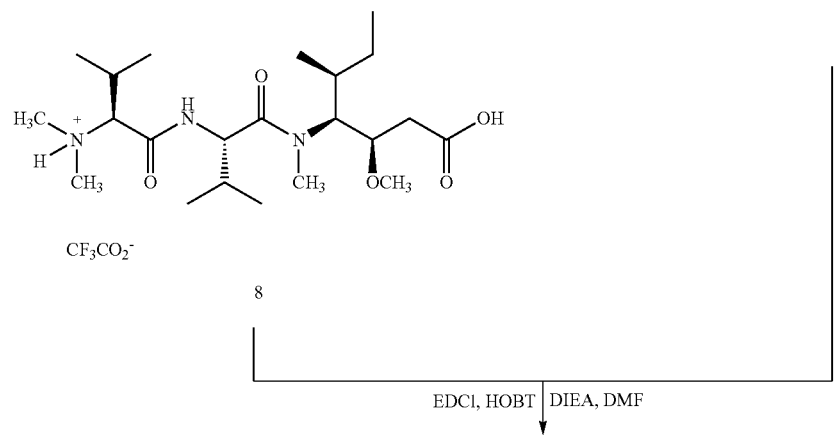

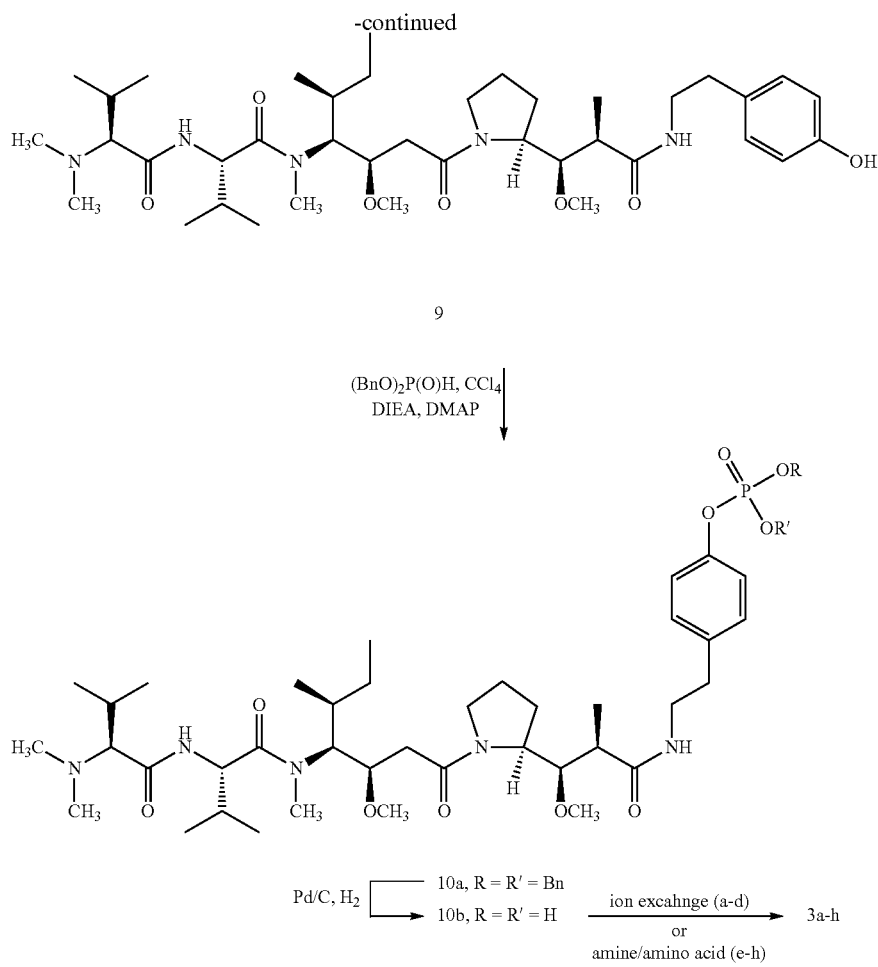

Formation of phosphate diester 10a was achieved via in situ generation of dibenzyl chlorophosphate, from reaction of dibenzyl phosphite and carbon tetrachloride, and was followed by removal of the benzyl ester groups by hydrogenolysis to provide the free phosphoric acid 10b. The pure 10b was quite unstable but could be stored for short periods as a methanolic solution (<0.01 M at 4° C.) and was generally used immediately as follows to provide compounds 3a-h. The passage of acid 10b through a Dowex cation exchange resin ($Na^+$ form) provided the sodium salt (3b), and compounds 3a,c,d were similarly produced by ion exchange of the free acid or of either the sodium or potassium salts in the appropriate Dowex resin. The remaining salts (3e-h) were prepared directly from the free acid 10b by treatment with the appropriate base or amino acid. The solubilities of each salt and of precursor 9 were measured in distilled water at room temperature. The most soluble were the sodium (3b) and potassium (3c) salts (Table 2).

TABLE 2

Solubility of Compounds 3a-h and 10[a]

| compound no. | mg/mL |
| --- | --- |
| 3a | >65 |
| 3b | >236 |
| 3c | >120 |
| 3d | >72 |

TABLE 2-continued

Solubility of Compounds 3a-h and 10[a]

| compound no. | mg/mL |
| --- | --- |
| 3e | <5 |
| 3f | >51 |
| 3g | 7 |
| 3h | 7 |
| 9 | <1 |

[a]In distilled water at 23° C.

A similar convergent synthesis was planned for the preparation of the auristatin aminoquinoline modifications (4, 5), that is, formation of the Dap-aminoquinoline unit, followed by condensation with tripeptide 8. As shown in Scheme 2, Boc-Dap (6) and 2-aminoquinoline (2-AQ) were condensed to give Boc-Dap-2-AQ (11), diethylcyanophosphonate (DEPC) being used as coupling reagent, followed by deprotection to give the amine TFA salt (12). Coupling of 12 and 8 with use of DEPC gave the desired auristatin 2-AQ (4). The doubling of signals in the $^1$H NMR spectrum of 4 because of conformational changes was also noted.

SCHEME 2

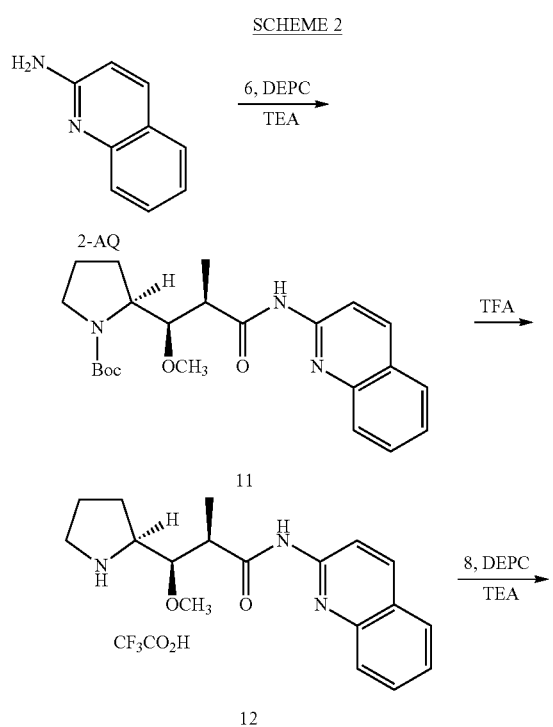

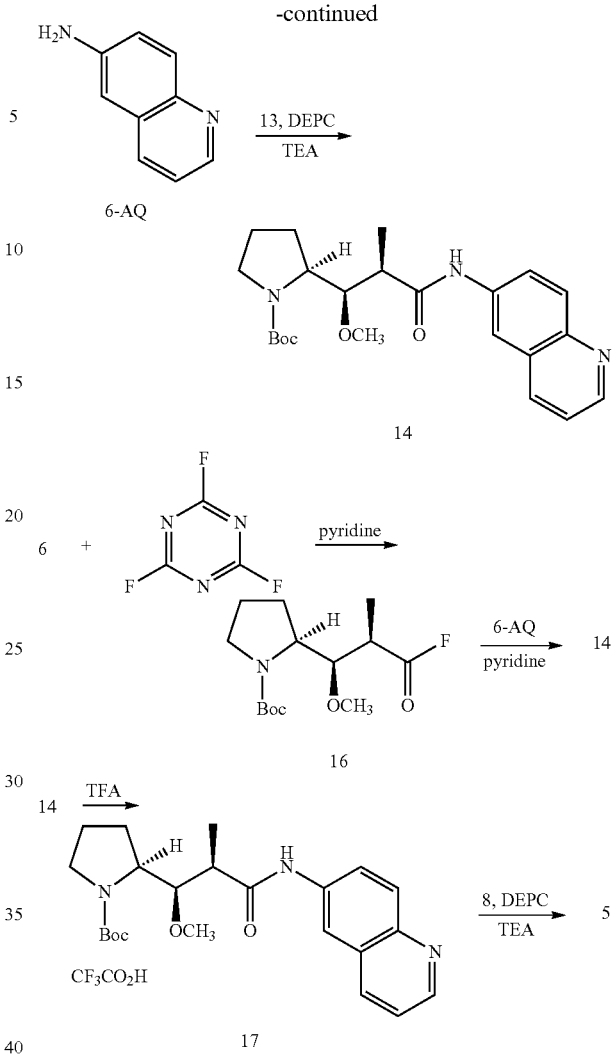

Preparation of auristatins from other aminoquinoline isomers proved more difficult. First, the coupling of 5-aminoquinoline (5-AQ) with compound 6 was attempted, but use of DEPC failed to give the desired product. The coupling agent PyBroP was next used under standard conditions, but only starting material (6 and 5-AQ) was detected after 100 h. The activity of the aminoquinolines varies with the position of the amino group,[3,4] and they are in general poor nucleophiles. Therefore, we considered a route involving an activated intermediate preformed from the amino acid. Pozdnev[5a] used di-tert-butyl dicarbonate (Boc anhydride, $Boc_2O$), in the presence of pyridine, to form activated esters of a number of protected amino acid derivatives, which were then condensed successfully with 6-aminoquinoline (6-AQ). Use of this method to couple 5-AQ and compound 6 failed, and was not further pursued, and the condensation of 6-aminoquinoline (6-AQ) with 6, via mixed anhydride 13 (Scheme 3), was next attempted.

SCHEME 3

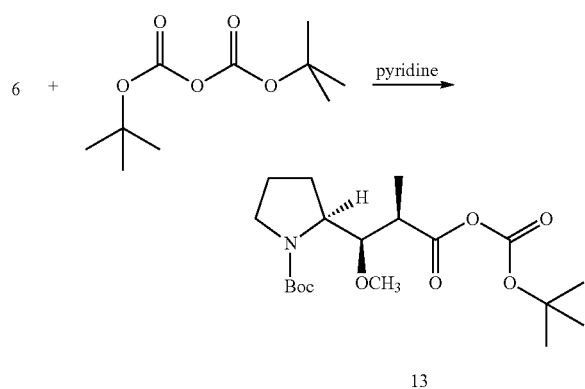

A mixture of $Boc_2O$ and 6 in pyridine and dimethylformamide (DMF) was allowed to stir for 10 min, and 6-AQ was then added.[5a] After isolation of products, the reaction was found to have given the desired Boc-Dap-6-AQ (14), along with Boc-6-AQ (at least half of the 6-AQ was used in formation of this product). When 6 and $Boc_2O$ were allowed to stir in base for an hour so that formation of ester 13 could go to completion (with evolution of $CO_2$) before addition of 6-AQ,[5b] formation of Boc-6-AQ was avoided, and in isolation of the desired product a citric acid wash was found useful for removal of unreacted aminoquinoline. However, the yield of product was still quite low, at 25%, and another method was sought.

Among the most reactive of the common activated intermediates are the amino acid fluorides,[6] which have been shown to be very efficient reagents for peptide bond formation.[7] With a sample of Boc-Dap-6-AQ (14) in hand for comparison, the condensation of the acid fluoride of 6 with 6-AQ was next attempted (Scheme 4). Reaction of cyanuric fluoride (15) with Boc-Dap (6) to give Boc-Dap-C(O)F (16) was carried out under mild conditions, and the crude product was used immediately in a condensation reaction with 6-AQ, in the presence of pyridine. The reaction did not go to completion (there was no detectable reduction in the amounts of unreacted compounds from 6 h to 20 h later), and the desired Boc-Dap-6-AQ (14) was isolated in 26% yield. Compound 14 was then treated with TFA to give the Dap-6-AQ.TFA salt (17), which was condensed with Dov-Val-Dil.TFA (8) to give auristatin-6-AQ (5).

In a repeat of the synthesis of acid fluoride 16, diisopropylethylamine (DIEA) was used as base, and purification of 16 was carried out on silica gel before condensation with 6-AQ, in the presence of DIEA, to give Boc-Dap-6-AQ (14). Reaction was slow, and at 44 h no change was apparent compared to the mixture at 32 h. The colorless oil that was isolated contained both product 14 and unreacted 16 (by tlc). According to the literature, the reaction of Fmoc amino acid fluorides with amines is often very slow and is not dependent on base[7b,c] (the presence of base can increase the reaction rate but lack of it can result in a cleaner reaction). Of the two methods to synthesize Boc-Dap-6-AQ (5), use of $Boc_2O$ to form active intermediate 13 led consistently to a yield of about 24%, whereas the yield from the Boc-Dap-C(O)F (16) method varied from 26% (using pyridine) to 6.6% (using DIEA and purifying the intermediate).

Compounds 3b, 3c, 4, 5 and 9 were evaluated against the murine P388 lymphocytic leukemia cell line and showed exceptional activity; auristatins 3b, 4, and 5 were also tested against a minipanel of human cancer cell lines in our laboratories, with similarly strong activity evident (Table 3), especially from compounds 3b and 5. These in vitro data are quite comparable to those of dolastatin 10 (1) and auristatin PE (2a), each of which had $GI_{50}$ values of $10^{-5}$-$10^{-6}$ μg/mL ($10^{-2}$-$10^{-3}$ nM) against a similar minipanel of human cell lines.[8a,b,9]

(2) Pettit, G. R.; Srirangam, J. K.; Singh, S. B.; Williams, M. D.; Herald, D. L.; Barkóczy, J.; Kantoci, D.; Hogan, F. *J. Chem. Soc., Perkin Trans. 1* 1996, 859-863.

(3) Egan, T. J.; Hunter, R.; Kaschula, C. H.; Marques, H. M.; Misplon, A.; Walden, J. *J. Med. Chem.* 2000, 43, 283-291

(4) (a) Schulman, S. G.; Abate, K.; Kovi, P. J.; Capomacchia, A. C.; Jackman, D. *Anal. Chim. Acta* 1973, 65, 59-67. (b) Abernethy, J. L.; Kilday, W. *J. Org. Chem.* 1960, 25, 1924-1928.

(5) (a) Pozdnev, V. F. *Int. J. Peptide Protein Res.* 1994, 36-48. (b) Furlong, S. T.; Mauger, R. C.; Strimpler, A. M.; Liu, Y.-P.; Morris, F. X.; Edwards, P. D. *Bioorg. Med. Chem.* 2002, 10, 3637-3647.

(6) (a) Olah, G. A.; Nojima, M.; Kerekes, I. *Synthesis* 1973, 487-488. (b) Bertho, J.-N.; Loffet, A.; Pinel, C.; Reuther, F.; Sennyey, G. *Tetrahedron Lett.* 1991, 32, 1303-1306.

(7) (a) Carpino, L. A.; Mansour, E.-S. M. E.; Sadat-Aalee, D. *J. Org. Chem.* 1991, 56, 2611-2614. (b) Wenschuh, H.; Beyermann, M.; El-Faham, A.; Ghassemi, S.; Carpino, L. A.; Bienert, M. *J. Chem. Soc., Chem. Commun.* 1995, 669-670. (c) Carpino, L. A.; Beyermann, M.; Wenschuh, H.; Bienert, M. *Acc. Chem. Res.* 1996, 29, 268-274.

(8) (a) Pettit, G. R. In *Progress in the Chemistry of Organic Natural Products*; Herz, W.; Kirby, G. W.; Moore, R. E.; Steglich, W.; Tamm, C., Eds.; Springer: Vienna, 1997; Vol. 70, 1-79. (b) Pettit, G. R.; Srirangam, J. K.; Barkoczy, J.; Williams, M. D.; Durkin, K. P. M.; Boyd, M. R; Bai, R.; Hamel, E.; Schmidt, J. M.; Chapuis, J.-C. *Anti-Cancer Drug Des.* 1995, 10, 529-544.

TABLE 3

Murine and Human Cancer Cell Line Results [$ED_{50}$ and $GI_{50}$, μg/mL (nM)][a]

| compound number | cell line[b] | | | | | | |
|---|---|---|---|---|---|---|---|
| | P388 | NCI-H460 | KM20L2 | DU-145 | BXPC-3 | MCF-7 | SF-268 |
| 3b | <0.001 | 0.00088 | 0.00061 | 0.00054 | 0.046 | 0.00068 | 0.00125 |
| | (<1.2) | (1.05) | (0.72) | (0.64) | (54.6) | (0.81) | (1.48) |
| 3c | 0.0076 | | | | | | |
| | (8.7) | | | | | | |
| 4 | 0.031 | 0.016 | 0.0077 | 0.023 | 0.029 | 0.0046 | 0.029 |
| | (42.8) | (22.1) | (10.6) | (31.8) | (40.1) | (6.35) | (40.1) |
| 5 | 0.0026 | 0.00036 | 0.00025 | 0.00030 | 0.00031 | 0.00014 | 0.00016 |
| | (3.59) | (0.50) | (0.35) | (0.41) | (0.43) | (0.19) | (0.22) |
| 9 | 0.0036 | | | | | | |
| | (5.0) | | | | | | |

[a]Cytotoxicity concentrations as nanomolar values are given in parentheses.
[b]Cancer cell lines in order: murine lymphocytic leukemia (P388); lung (NCI-H460); colon (KM20L2); prostate (DU-145); pancreas (BXPC-3); breast (MCF-7); CNS (SF-268).

As shown in Table 2, auristatin TP as sodium phosphate 3b ($GI_{50}$ $10^{-2}$-$10^{-4}$ μg/mL), auristatin 2-AQ (4, $GI_{50}$ $10^{-2}$-$10^{-3}$ μg/mL), and auristatin 6-AQ (5, $GI_{50}$ $10^{-4}$ μg/mL), exhibited superior cancer cell growth inhibitory properties.

REFERENCES EMPLOYED FOR METHODS AND BACKGROUND (1) (a) Pettit, G. R.; Singh, S. B.; Herald, D. L.; Lloyd-Williams, P.; Kantoci, D.; Burkett, D. D.; Barkóczy, J.; Hogan, F.; Wardlaw, T. R. *J. Org. Chem.* 1994, 59, 6287-6295. (b) Pettit, G. R.; Grealish, M. P. *J. Org. Chem.* 2001, 66, 8640-8642. (c) Mordant, C.; Reymond, S.; Tone, H.; Layergne, D.; Touati, R.; Ben Hassine, B.; Ratovelomanana-Vidal, V; Genet, J.-P. *Tetrahedron* 2007, 63, 6115-6123.

(9) Pettit, G. R. Dolastatin anticancer drugs. In *International Oncology Updates: Marine anticancer compounds in the era of targeted therapies*; Chabner, B.; Cortés-Funes, H., Eds.; Permanyer Publications: Barcelona, 2009.

While particular materials, formulations, operational sequences, process parameters, and end products have been set forth to describe and exemplify this invention, they are not intended to be limiting. Rather, it should be noted by those ordinarily skilled in the art that the written disclosures are exemplary only and that various other alternatives, adaptations, and modifications may be made within the scope of the present invention. Accordingly, the present invention is not limited to the specific embodiments illustrated herein, but is limited only by the following claims.

What is claimed is:

1. A compound of formula (I):

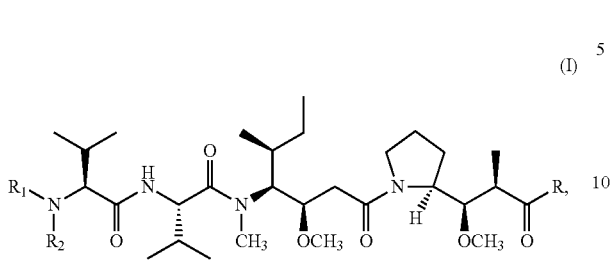

wherein R is selected from the group consisting of:

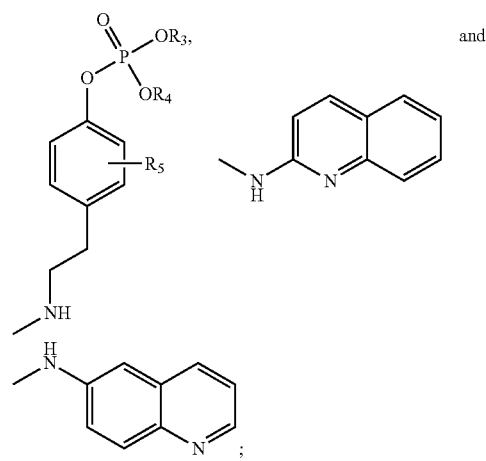

R$_1$ and R$_2$ are independently selected from the group consisting of H, alkyl, alkenyl, alkynyl and a Linker Unit;

R$_3$ and R$_4$ are independently selected from the group consisting of lithium (Li$^+$), sodium (Na$^+$), potassium (K$^+$), hydrogen (H), morpholine, quinine, tris(hydroxymethyl)aminomethane (TRIS), serine, nitroarginine and a Linker Unit; and each R$_5$ is selected from the group consisting of H, alkyl, alkenyl, alkynyl and a Linker Unit.

2. The compound of claim 1, wherein R is:

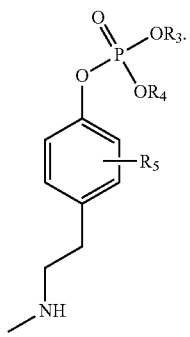

3. The compound of claim 2, wherein R$_3$ and R$_4$ are sodium.

4. The compound of claim 3, wherein R$_5$ is H.

5. The compound of claim 1, wherein R is

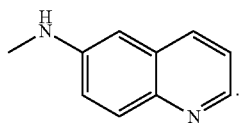

6. The compound of claim 1, wherein R is

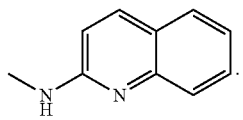

7. The compound of claim 1, wherein R$_1$ is methyl and R$_2$ is methyl.

8. The compound of claim 1, wherein one of R$_1$ or R$_2$ is a Linker Unit.

9. The compound of claim 8, wherein the Linker Unit comprises an antibody.

10. A pharmaceutical composition comprising a compound of claim 1 or a pharmaceutically acceptable salt thereof and a pharmaceutically acceptable carrier.

11. A pharmaceutical composition comprising a combination of compounds of claim 1 or pharmaceutically acceptable salts thereof and a pharmaceutically acceptable carrier.

12. The pharmaceutical composition of claim 10 or claim 11, further comprising a therapeutically effective amount of chemotherapeutic agent selected from the group consisting of a tubulin-forming inhibitor, a topoisomerase inhibitor, and a DNA binder.

13. A method for killing or inhibiting the proliferation of tumor cells or cancer cells comprising treating tumor cells or cancer cells with a compound of claim 1, or a pharmaceutically acceptable salt or solvate thereof, in an amount effective to kill or inhibit the proliferation of the tumor cells or cancer cells.

14. A method for treating cancer in a patient comprising administering to the patient a compound of claim 1, or a pharmaceutically acceptable salt or solvate thereof, wherein the compound is administered in an amount effective to treat cancer.

15. The method of claim 12, further comprising administering an effective amount of a chemotherapeutic agent.

16. The method of claim 13 or 14, wherein the compound is in a formulation comprising a pharmaceutically acceptable carrier.

17. A method of inhibiting the growth of tumor cells that overexpress a tumor-associated antigen comprising administering to a patient the compound of claim 1 conjugated to an antibody that is specific for said tumor-associated antigen, and optionally a chemotherapeutic agent wherein the compound and said chemotherapeutic agent are each administered in amounts effective to inhibit growth of tumor cells in the patient.

18. The method of claim 17, wherein the compound sensitizes the tumor cells to said chemotherapeutic agent.

19. The method of claim 17, wherein the compound induces cell death.

20. The method of claim 17, wherein the compound induces apoptosis.

21. The method of claim 17, wherein the cancer is selected from the group consisting of breast, ovarian, stomach, endometrial, salivary gland, lung, kidney, colon, colorectal, thyroid, pancreatic, prostate and bladder cancer.

22. An article of manufacture comprising the compound of claim 1, a container, and a package insert or label indicating that the compound can be used to treat cancer characterized by the overexpression of at least one tumor-associated antigen.

* * * * *

UNITED STATES PATENT AND TRADEMARK OFFICE
CERTIFICATE OF CORRECTION

PATENT NO. : 9,044,518 B2  
APPLICATION NO. : 14/007743  
DATED : June 2, 2015  
INVENTOR(S) : George R. Pettit et al.

It is certified that error appears in the above-identified patent and that said Letters Patent is hereby corrected as shown below:

In the Specification:

Column 1, lines 45-48, please delete "This invention was made with government support from grants R01 CA 90441-01-05, 2R56 CA 090441-06A1, and 5-R01 CA 90441-07-08 awarded by the Division of Cancer Treatment and Diagnosis, National Cancer Institute, DHHS." and substitute therefor -- This invention was made with government support under grant number R01 CA090441 awarded by the National Institutes of Health. --.

Signed and Sealed this  
Twenty-sixth Day of July, 2016

Michelle K. Lee  
*Director of the United States Patent and Trademark Office*